United States Patent
Pennington et al.

(10) Patent No.: US 11,825,839 B2
(45) Date of Patent: Nov. 28, 2023

(54) CRYOPRESERVATION OF CELL-SEEDED SUBSTRATES AND RELATED METHODS

(71) Applicants: University of Southern California, Los Angeles, CA (US); The Regents of the University of California, Oakland, CA (US)

(72) Inventors: Britney O. Pennington, Orlando, FL (US); Jeffrey K. Bailey, Goleta, CA (US); Mohamed A. Faynus, Brampton (CA); Cassidy Arnold, Goleta, CA (US); Lincoln V. Johnson, Santa Barbara, CA (US); Dennis O. Clegg, Ventura, CA (US); Mark S. Humayun, Glendale, CA (US); David R. Hinton, Venice, CA (US); Danhong Zhu, Covina, CA (US); Debbie Mitra, Altadena, CA (US)

(73) Assignees: University of Southern California, Los Angeles, CA (US); The Regents of the University of California, Oakland, CA (US)

( * ) Notice: Subject to any disclaimer, the term of this patent is extended or adjusted under 35 U.S.C. 154(b) by 726 days.

(21) Appl. No.: 16/557,897

(22) Filed: Aug. 30, 2019

(65) Prior Publication Data

US 2020/0077641 A1   Mar. 12, 2020

Related U.S. Application Data

(60) Provisional application No. 62/728,646, filed on Sep. 7, 2018.

(51) Int. Cl.
*C12N 5/079* (2010.01)
*C08G 61/02* (2006.01)
*A01N 1/02* (2006.01)

(52) U.S. Cl.
CPC .......... *A01N 1/021* (2013.01); *C12N 5/0621* (2013.01); *C08G 61/025* (2013.01)

(58) Field of Classification Search
None
See application file for complete search history.

(56) References Cited

U.S. PATENT DOCUMENTS

| | | | |
|---|---|---|---|
| 4,163,828 A | 8/1979 | Mahoney | |
| 7,923,823 B2 | 4/2011 | Mengel et al. | |
| 8,877,489 B2 | 11/2014 | Tai et al. | |
| 9,095,524 B2 | 8/2015 | Warnke et al. | |
| 10,470,457 B2 * | 11/2019 | Zhu | A61L 27/34 |
| 2003/0054331 A1 | 3/2003 | Fraser et al. | |
| 2005/0106554 A1 | 5/2005 | Palecek et al. | |
| 2006/0063141 A1 | 3/2006 | Mcgann et al. | |
| 2009/0123992 A1 | 5/2009 | Chin | |
| 2009/0130756 A1 | 5/2009 | Klann et al. | |
| 2012/0009159 A1 | 1/2012 | Humayun et al. | |
| 2013/0143326 A1 | 6/2013 | Tai et al. | |
| 2014/0045264 A1 | 2/2014 | Zhu et al. | |
| 2017/0067017 A1 | 3/2017 | Meyer et al. | |

FOREIGN PATENT DOCUMENTS

| | | |
|---|---|---|
| EP | 2702135 A2 | 3/2014 |
| EP | 2702135 | 4/2019 |
| JP | 2003047464 | 2/2003 |
| JP | 2007306856 | 11/2007 |
| JP | 2014512820 | 5/2014 |
| JP | 6200883 | 9/2017 |
| WO | 2005069766 | 8/2005 |
| WO | 2007058308 | 5/2007 |
| WO | 2012149484 | 11/2012 |
| WO | 2014121077 | 8/2014 |

OTHER PUBLICATIONS

Foltz & Clegg Rapid, Directed Differentiation of Retinal Pigment Epithelial Cells from Human Embryonic or Induced Pluripotent Stem Cells, 2017, J Vis Exp, (128) e56274: 1-6. (Year: 2017).*

Amps et al., "In Situ Cryopreservation of Human Embryonic Stem Cells in Gas-permeable Membrane Culture Cassettes for High Post-thaw Yield and Good Manufacturing Practice", Cryobiology, vol. 60, No. 3, Jun. 1, 2010, pp. 1-7.

Chang et al., "Cell and Protein Compatibility of Parylene-C Surfaces", Langmuir, vol. 2, No. 23, Oct. 4, 2007, 8 pages.

EP12776772.1 , "Extended European Search Report", dated Jan. 7, 2015, 9 pages.

Katkov et al., "DMSO-Free Programmed Cryopreservation of Fully Dissociated and Adherent Human Induced Pluripotent Stem Cells", Stem Cells International, vol. 18, Jan. 1, 2011, 8 pages.

Li et al., "Cryopreservation of Human Embryonic Stem Cells with a New Bulk Vitrification Method", Biology of Reproduction, vol. 82, No. 5, Jan. 14, 2010, pp. 848-853.

Lu et al., "Mesh-Supported Submicron Parylene-C Membranes for Culturing Retinal Pigment Epithelial Cells", Biomedical Microdevices, vol. 14, No. 4, 2012, pp. 659-667.

Morris et al., "Cryopreservation of Murine Embryos, Human Spermatozoa and Embryonic Stem Cells Using a Liquid Nitrogen-free, Controlled Rate Freezer", Reproductive Bio Medicine Online, vol. 13, No. 3, Jun. 23, 2006, pp. 421-426.

Nie et al., "Scalable Culture and Cryopreservation of Human Embryonic Stem Cells on Microcarriers", Biotechnology Progress, American Institute of Chemical Engineers, vol. 25, No. 1, Jan. 1, 2009, pp. 20-31.

(Continued)

*Primary Examiner* — Teresa E Knight
(74) *Attorney, Agent, or Firm* — Mark P. Mathison

(57) ABSTRACT

Disclosed herein are methods and compositions for the identification of viability enhancing cell features and substrate features as they relate to post-cryopreservation survival of substrate seeded cells. Embodiments of the present invention further involve identification of cell features to manufacture a supernatant that is useful for cell culturing and treatment of various diseases.

20 Claims, 18 Drawing Sheets

(56) References Cited

OTHER PUBLICATIONS

PCT/US2012/035676, "International Preliminary Report on Patentability", dated Nov. 7, 2013, 6 pages.
PCT/US2012/035676, "International Search Report and Written Opinion", dated Oct. 31, 2012, 8 pages.
PCT/US2019/049230, "International Preliminary Report on Patentability", dated Mar. 18, 2021, 14 pages.
Pereira-Rodrigues et al., "Modulation of Hepatocarcinoma Cell Morphology and Activity by Parylene-C Coating on PDMS", PLoS One, vol. 5, No. 3, Mar. 16, 2010, 13 pages.
Dutt et al., "RPE-Secreted Factors: Influence Differentiation in Human Retinal Cell Line in Dose- and Density-Dependent Manner", Journal of Ocular Biology, Diseases, And Informatics, vol. 3, No. 4, Jan. 12, 2012, pp. 144-160.
Jinno et al., "Microfabricated Multilayer Parylene-C Stencils for the Generation of Patterned Dynamic Co-Cultures", Journal of Biomedical Materials Research Part A, vol. 86, No. 1, Apr. 28, 2008, pp. 278-288.
Lu et al., "Ultrathin Parylene-C Semipermeable Membranes for Biomedical Applications", IEEE 24th International Conference on Micro Electro Mechanical Systems, MEMS, Jan. 2011, pp. 505-508.
PCT/US2019/049230, "International Search Report and Written Opinion", dated Feb. 5, 2020, 20 pages.
PCT/US2019/049230, "Invitation to Pay Additional Fees and, Where Applicable, Protest Fee", dated Dec. 13, 2019, 15 pages.
Teshima et al., "Pairing Single Adherent Cells in the Dynamic Microarray", IEEE 24th International Conference on Micro Electro Mechanical Systems, MEMS, Jan. 2011, pp. 71-74.

\* cited by examiner

CRYOPRESERVATION OF CELL-SEEDED SUBSTRATES AND RELATED METHODS

CROSS-REFERENCES TO RELATED APPLICATIONS

This application claims the benefit of U.S. Provisional Application No. 62/728,646, filed Sep. 7, 2018, which is hereby incorporated by reference in its entirety for all purposes.

STATEMENT AS TO RIGHTS TO INVENTIONS MADE UNDER FEDERALLY SPONSORED RESEARCH AND DEVELOPMENT

Not Applicable

BACKGROUND

1. Field of Invention

The present application relates generally to instruments and methods for the implantation of ultrathin substrates into target tissues, the ultrathin substrates being suitable for seeding with stem cells for stem cell therapy, microbubbles, and infused gels for drug delivery, among other therapeutic treatments. The ultrathin substrates may further be used for reproducible culturing of cells and cryopreservation once seeded with cells.

2. Description of Related Art

The scope of human disease that involves loss of, or damage to, cells is vast and includes, but is not limited to, ocular disease, neurodegenerative disease, endocrine disease, cardiovascular disease, and cancers. Cellular therapy involves the use of cells to treat diseased or damaged tissues. It is rapidly coming to the forefront of technologies that are poised to treat many diseases, in particular those that affect individuals who are non-responsive to traditional pharmacologic therapies. Many of these diseases would benefit from long term concentrated target-area treatment, which would reduce systemic side effects. However, certain drugs, such as protein therapeutics, are expensive, costing thousands of dollars per vial and require repetitive treatments with no end.

In fact, many diseases that are candidates for application of cellular therapy are not fatal, but involve loss of normal physiological function. For example, ocular diseases often involve functional degeneration of various ocular tissues which affects the vision, and thus the quality of life of numerous individuals.

The mammalian eye is a specialized sensory organ capable of converting incoming photons focused by anterior optics (cornea and lens) into a neurochemical signal. This process of phototransduction allows for sight by sending action potentials to higher cortical centers via the optic nerve. The retina of the eye comprises photoreceptors that are sensitive to various levels of light and interneurons that relay signals from the photoreceptors to the retinal ganglion cells. These photoreceptors are the most metabolically active cells in the eye (if not the body), and are supported metabolically and functionally by retinal pigment epithelial (RPE) cells. These RPE cells are positioned in a monolayer in the eye and are critical to vision.

Numerous pathologies can compromise or entirely eliminate an individual's ability to perceive visual images, including trauma to the eye, infection, degeneration, vascular irregularities, and inflammatory problems. The central portion of the retina is known as the macula, which is responsible for central vision, fine visualization and color differentiation. The function of the macula may be adversely affected by age related macular degeneration (wet or dry), diabetic macular edema, idiopathic choroidal neovascularization, high myopia macular degeneration, or advanced retinitis pigmentosa, among other pathologies.

Age-related macular degeneration typically causes a loss of vision in the center of the visual field (the macula) because of damage to the retina. It is a major cause of visual impairment in older adults (>50 years of age). Macular degeneration occurs in "wet" and "dry" forms.

In the dry form, cellular debris (drusen) accumulates between the RPE cell layer and the choroid, which adversely affects the RPE cells leading to their dysfunction, degeneration and, ultimately, death. The photoreceptor cells of the retina that depend on viable RPE cells to perform crucial support functions become dysfunctional and die secondary to the RPE cell pathology.

In the more severe wet form, newly formed blood vessels from the choroid infiltrate the space behind the macula; the newly formed blood vessels are fragile and often leak blood—thereby causing the death of photoreceptors and their supporting cells.

While diseases that cause damage to specific cells or tissues are clear candidates for cellular therapy, there remains a need in the art for improved methods of cellular therapy, which include methods, substrates, and tools to improve the efficacy of cellular therapy, as well as methods and compositions allowing for long term storage of functional and viable cells to be used in such therapies.

BRIEF SUMMARY

In various embodiments, the present invention relates generally to methods and compositions for the cryopreservation of cells grown on a substrate. In particular, methods and compositions for the cryopreservation of cells seeded and/or grown on a polymeric substrate. In certain applications, the cells are retinal pigment epithelial (RPE) cells, photoreceptor cells, stem cells, pre-differentiated cells, differentiations of such cells, or a combination thereof, regardless of the differentiation, derivation or culture history of the cells.

To address the need for improved long term storage of cell-containing compositions for use in cell therapy, there is provided in some embodiments, a method of cryopreserving cells on a substrate comprising exposing a substrate seeded with a composition of cells to a temperature ramp-down phase having a desired temperature reduction rate, transferring the cell-seeded substrate to a desired intermediate temperature range for a first period of time, and maintaining the cell-seeded substrate at a desired storage temperature range for a second period of time, resulting in cryopreserved cells on a substrate that are suitable for long term storage and later use in cell therapy after thawing.

The present invention provides, in various embodiments, specific cryopreservation methods and variations of procedural steps to accommodate a variety of cell characteristics. Additionally, specific cell characteristics and substrate characteristics are selected at various stages of the cryopreservation process to improve the cell viability and implant success of the cell seeded substrate for efficacious treatment.

The present inventions introduce new methods and apparatus that provide many advantages including beneficial outcomes for cryopreservation of substrates including higher cell survival, minimal damage to substrates, and an overall simplified process for generating cell seeded substrates suitable for cell growth and direct implantation.

In another aspect, the invention introduces methods of intentional suppression of melanogenesis. Such methods may be enabled by specific items included in a kit.

The present invention also introduces new methods of forming cell specific culture media to improve cell growth, cell growth rate, viability, and differentiation. In certain embodiments, such cell specific culture mediums may be extracted and further be adapted for direct injections such as intravitreal (IVT) delivery to a region of the specific cells or an already implanted cell seeded substrate.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method of cryopreserving cells on a substrate, the method including: providing a biocompatible polymer substrate seeded with a monolayer of immature retinal pigment epithelium (rpe) cells, the polymer substrate providing a cell seeding surface. The method of cryopreserving cells also includes identifying when i) the monolayer of immature rpe cells reaches between 90% and 99% confluence on the substrate and ii) most of the immature rpe cells are not fully pigmented. The method of cryopreserving cells also includes exposing, upon the identifying, the substrate seeded with cells to a controlled temperature reduction rate between about −1 c per minute to about −30 c per minute until a first temperature below −20 c is reached; Other embodiments of this aspect include corresponding computer systems, apparatus, and computer programs recorded on one or more computer storage devices, each configured to perform the actions of the methods.

Implementations may include one or more of the following features. The method where the cell-seeded substrate reaches a temperature below that which delineates a latent heat release of the seeded cells. The method where a surface of the is substantially parallel to the monolayer of the immature rpe cells seeded on the substrate, sufficient to induce nucleation and efficient temperature compensation in response to the latent heat release of the seeded cells. The method further including: maintaining the cell-seeded substrate at the first temperature, the first temperature being between −20 c to about −100 c after the controlled temperature reduction rate for a first period of time to obtain uniformity of temperature. The method may also include maintaining the cells at a storage temperature lower than the first temperature for a second period of time within 50c of the first temperature, thereby obtaining cryopreserved cells. The method further including: maintaining the cell-seeded substrate at the first temperature, the first temperature being between −20 c to about −100 c after the controlled temperature reduction rate for a first period of time. The method may also include conducting a second controlled temperature reduction rate to finally maintain the cells at a storage temperature below −196 c for a second period of time, thereby obtaining cryopreserved cells. The method where the second period of time is between 24 hours and 60 months. The method where the second controlled temperature reduction rate is between about −1 c per minute to about −30 c per minute. The method where the monolayer of cells have a cell seeding density between 200,000 and 700,000 cells per milliliter of cell suspension, or between 100,000 and 350,000 cells per square centimeter of substrate surface. The method where over 50% of the rpe cells have a cobblestone morphology. The method where the rpe cells have no pigmentation or partial pigmentation. The method where the cells are rpe cells exhibiting cryopreservation viability characteristics selected from: (i) non-pigmented or partially pigmented rpe cells, (ii) adhered but non-polarized, partially polarized, or fully polarized rpe cells, (iii) rpe cells with or without mature cobblestone morphology, (iv) rpe cells with gene expression levels below that of mature cells or lacking specific gene expression, and (v) rpe cells in a confluent or subconfluent over 90% monolayer configuration. The method where the substrate has one or more characteristics selected from: (i) a coefficient of thermal expansion of the substrate, (ii) a substrate elasticity parameter, (iii) a substrate thickness, (iv) surface modification, (v) shear force resistance, said characteristics helping to enhance viability of the seeded cells and functionality of the substrate during cryopreservation and thawing. The method where the biocompatible polymer includes parylene. The method where the identifying includes determining when at least one or more apical secretions, basal secretions, or non-polar specific secretions of the immature rpe cells at levels below that of mature rpe cells. The method where the apical secretions include ab crystallin, hyaluronan, matrix metallopeptidase (mmp)-9, pigment epithelium-derived factor (pedf), transforming growth factor (tgf)-β, tissue inhibitors of metalloproteinases (timp)-i, or mechano growth factor (mgf)-e8. The method where the basal secretions include cystatin c, endothelin i, fibroblast growth factor (fgf) 5, or vascular endothelial growth factor (vegf). The method where the non-polar specific secretions include brain-derived neurotrophic factor (bdnf), complement factor h (cfh), ciliary neurotrophic factor (cntf), fibulin 3/5, fibroblast growth factor (fgf) 2, heparin binding-epidermal growth factor (hb-egf), hepatocyte growth factor (hgf), insulin-like growth factor (igf)-i, leukemia inhibitory factor (lif), matrix metalloproteinase (mmp)-9, nerve growth factor (ngf), tropoelastin. The method the identifying includes determining gene expression of immature rpe cells of at least one or more of rpe65, rex1, eif2b2, serf2, ube2r2 to be below that of mature rpe cells. The method where the substrate includes thin regions configured to allow the cells to diffuse nutrients therethrough. Implementations of the described techniques may include hardware, a method or process, or computer software on a computer-accessible medium.

One general aspect includes a method of generating an implantable cell seeded substrate the method including: providing a biocompatible polymer substrate seeded with a monolayer of immature retinal pigment epithelium (rpe) cells, the polymer substrate providing a cell seeding surface. The method also includes cryopreserving cells on the substrate by exposing the substrate seeded with cells to a controlled temperature reduction rate between about −1 c per minute to about −30 c per minute. The method also includes transferring the cell seeded substrate to a temperature below 4 c, thereby obtaining cryopreserved or hibernated cells. The method also includes thawing the cryopreserved cells on said substrate by warming the cell seeded substrate to a target temperature using a temperature ramp-up heating rate to obtain thawed cells seeded on the substrate, where the thawed cells retain viability and/or functionality post-thaw. The method also includes culturing the seeded cells for an additional period of time to reach a mature state prior to implantation. Other embodiments of this aspect include corresponding computer systems, apparatus, and computer programs recorded on one or more computer storage devices, each configured to perform the actions of the methods.

Implementations may include one or more of the following features. The method further including: culturing the post-thaw substrate seeded cells in a first medium including a basal medium supplemented with a combination of including of at least one or more of bovine serum albumin (bsa), activin a, hepatocyte growth factor (fgf), insulin-like growth factor (igf) 1, dickkopf-related protein 1 (dkk1), and noggin. The method further including: culturing the post-thaw substrate seeded cells in a first medium including a basal medium supplemented by supernatant derived from previously cultured rpe cells and subsequently culturing the cells in a second medium including a basal medium supplemented with insulin-like growth factor (ifg) 1, dickkopf-related protein 1 (dkk1), and noggin. The method where the supernatant in the first medium is derived from the culturing of immature rpe cells that includes rpe cells exhibiting optimal cryopreservation viability characteristics selected from: (i) non-pigmented or partially pigmented rpe cells, (ii) non-polarized or partially polarized rpe cells, (iii) rpe cells with or without least 50% t mature cobblestone morphology, (iv) rpe cells with gene expression levels below that of mature cells or lacking specific gene expression, and (v) rpe cells in a subconfluent or confluent monolayer configuration. The method where the supernatant in the first medium is derived from the culturing of rpe cells exhibiting mature characteristics selected from: (i) pigmented rpe cells, (ii) polarized rpe cells, (iii) rpe cells with mature cobblestone morphology, (iv) rpe cells with gene expression levels comparable to mature rpe cells, and (v) rpe cells in a confluent monolayer configuration. Implementations of the described techniques may include hardware, a method or process, or computer software on a computer-accessible medium.

One general aspect includes a method of producing a cell line specific culture medium or acellular therapy, the method including: culturing immature rpe cells on a growth support structure; the rpe cells exhibiting optimal cryopreservation viability characteristics selected from: (i) non-pigmented rpe cells, (ii) non-polarized or partially polarized rpe cells, (iii) rpe cells without mature cobblestone morphology, (iv) rpe cells with gene expression levels below that of mature cells or lacking specific gene expression, and (v) rpe cells in a subconfluent monolayer configuration. The method also includes collecting media containing secreted factors. The method also includes purifying the media to create the culture medium or acellular therapy. Other embodiments of this aspect include corresponding computer systems, apparatus, and computer programs recorded on one or more computer storage devices, each configured to perform the actions of the methods.

Implementations may include one or more of the following features. The method further including: culturing the rpe cells until the cells exhibit mature characteristics selected from: (i) pigmented rpe cells, (ii) polarized rpe cells, (iii) rpe cells with mature cobblestone morphology, (iv) rpe cells with gene expression levels similar to mature cells, and (v) rpe cells in a confluent monolayer configuration, prior to purifying the media. The method where purifying is accomplished by centrifugal filtration, fractionation, size exclusion chromatography, affinity chromatography, size-exclusion filtration, or precipitation. The method further including: packaging the supernatant media in a syringe. The method where the supernatant is supplemented by a drug vehicle or diluent. The method further including: culturing photoreceptor cells or photoreceptor progenitor cells. The method where the growth support structure includes a substrate, a lattice structure, agar, or a hydrogel. The method where the cells are grown on, in, or encapsulated in a biocompatible substrate or container. Implementations of the described techniques may include hardware, a method or process, or computer software on a computer-accessible medium.

One general aspect includes the method for treating a disease or disorder, including: administering to a subject an effective amount of rpe cell specific culture medium or acellular therapy obtained by a method including. The method also includes culturing rpe cells on a growth support structure, the rpe cells exhibiting mature characteristics as characterized by rpe65 level detection. The method also includes collecting media containing secreted factors. The method also includes purifying the media to create the culture medium or acellular therapy. Other embodiments of this aspect include corresponding computer systems, apparatus, and computer programs recorded on one or more computer storage devices, each configured to perform the actions of the methods.

Implementations may include one or more of the following features. The method further including: transplanting the rpe cells. The method further including: transplanting rpe cells seeded onto a substrate. The method further including: transplantating photoreceptor cells. The method further including: transplantating the rpe cells and photoreceptor cells onto a substrate. The method where purifying is accomplished by centrifugal filtration, fractionation, size exclusion chromatography, affinity chromatography, size-exclusion filtration, or precipitation. The method where the growth support structure may be a substrate, a lattice structure, agar, or a hydrogel. The method where the cells are grown on, in, or encapsulated in a biocompatible substrate or container. Implementations of the described techniques may include hardware, a method or process, or computer software on a computer-accessible medium.

One general aspect includes a substrate for cellular therapy to generate an external limiting membrane of the retinal anatomy including: a substrate with a normal state or flexible state curvature and size substantially similar to that of a diseased portion of functional external limiting membrane of a patient. The substrate also includes rpe cells and photoreceptor cells seeded on the substrate as independent individual layers which post-implantation mature to generate an external limiting membrane. Other embodiments of this aspect include corresponding computer systems, apparatus, and computer programs recorded on one or more computer storage devices, each configured to perform the actions of the methods.

Implementations may include one or more of the following features. The substrate where the substrate is coated with media to attract the patient's precursor cells post-implantation to generate the external limiting membrane. The substrate further including a supernatant media manufactured by: culturing rpe cells on a growth support structure. The substrate may also include the rpe cells exhibiting mature characteristics as characterized by rpe65 level detection. The substrate may also include collecting media containing secreted factors. The substrate may also include purifying the media to create the culture medium or acellular therapy. Implementations of the described techniques may include hardware, a method or process, or computer software on a computer-accessible medium.

One general aspect includes a method of producing a cell specific culture medium including: culturing a first cell line on a selectively permeable substrate in a first culturing medium, where said first cell line processes the first culture medium and produces cell secretions. The method also includes collecting the cell secretions. The method also includes adding the cell secretions to a second culturing medium to form a cell specific culture medium. Other embodiments of this aspect include corresponding computer systems, apparatus, and computer programs recorded on one or more computer storage devices, each configured to perform the actions of the methods.

Implementations may include one or more of the following features. The method where the cell secretions include a combination of proteins, hormones, enzymes, byproducts and waste. The method where the cell secretions include apical secretion from rpe cells including at least one of: ab crystallin, hyaluronan, matrix metalloproteinase (mmp)-9, pigment epithelium-derived factor (pedf), transforming growth factor (tgf)-β, tissue inhibitors of metalloproteinases (timp)-i. The method where the cell secretions include basal secretion from rpe cells including at least one of: cystatin c, endothelin i, fibroblast growth factor (fgf) 5, vascular endothelial growth factor (vegf). The method where the cell secretions include non-polar specific secretion from rpe cells including at least one of: bdnf, cfh, cntf, fibulin 3/5, fgf 2, hb-egf, hgf, igf-i, lif, mmp-9, ngf, tropoelastin. The substrate induces polarity of seeded cells to allow for apical, basal, and non-polar specific secretions to be secreted. The cell specific culture medium formed is for controlled growth of non-mature rpe cells. The cell specific culture medium formed is for controlled maturation of non-mature rpe cells into mature rpe cells. The cell specific culture medium formed is formulated for intravitreal (ivt) injection. Implementations of the described techniques may include hardware, a method or process, or computer software on a computer-accessible medium.

One general aspect includes a method of forming a therapeutic composition including: culturing a first cell line on a selectively permeable substrate in a first culturing medium, where said first cell line processes the first culture medium and produces cell secretions. The method also includes collecting cell secretions. The method also includes purifying cell secretions by selecting specific cell secretions. Other embodiments of this aspect include corresponding computer systems, apparatus, and computer programs recorded on one or more computer storage devices, each configured to perform the actions of the methods.

Implementations may include one or more of the following features. The method further including: centrifuging one or more times at different speeds and reconstituting to create one or more pellets of varying compositions. The method further including fractionation, size exclusion chromatography, affinity chromatography, size-exclusion filtration, or precipitation. The method further including: reconstituting into different concentrations. The method where the formed therapeutic composition does not contain cells. Implementations of the described techniques may include hardware, a method or process, or computer software on a computer-accessible medium.

One general aspect includes a method of reversibly adhering a polymeric membrane onto another polymeric surface, including: placing the a membrane substantially surrounded by a volume of media on the another polymeric surface. The method also includes incrementally withdrawing a volume of media until the membrane's flat surface contacts a flat surface of another polymeric surface. The method also includes drying to reversibly adhere the membrane's flat surface to the contacting flat surface of another polymeric surface. Other embodiments of this aspect include corresponding computer systems, apparatus, and computer programs recorded on one or more computer storage devices, each configured to perform the actions of the methods.

Implementations may include one or more of the following features. The method where the polymeric surface is the bottom surface of a cell culture plate or well. The method where the media is Dulbecco's phosphate-buffered saline (dpbs). The method where the drying is conducted by a desiccator, temperature/humidity controlled chamber, baking in a drying oven, or leaving in a controlled room such as a clean room. The method where the polymeric membrane is parylene. The method further including introducing a volume of media to detach the membrane's flat surface from the contacting flat surface of another polymeric surface. Implementations of the described techniques may include hardware, a method or process, or computer software on a computer-accessible medium.

BRIEF DESCRIPTION OF THE DRAWINGS

The foregoing will be more readily understood from the following detailed description of the invention, in particular, when taken in conjunction with the drawings, in which.

DETAILED DESCRIPTION

Figure 1:
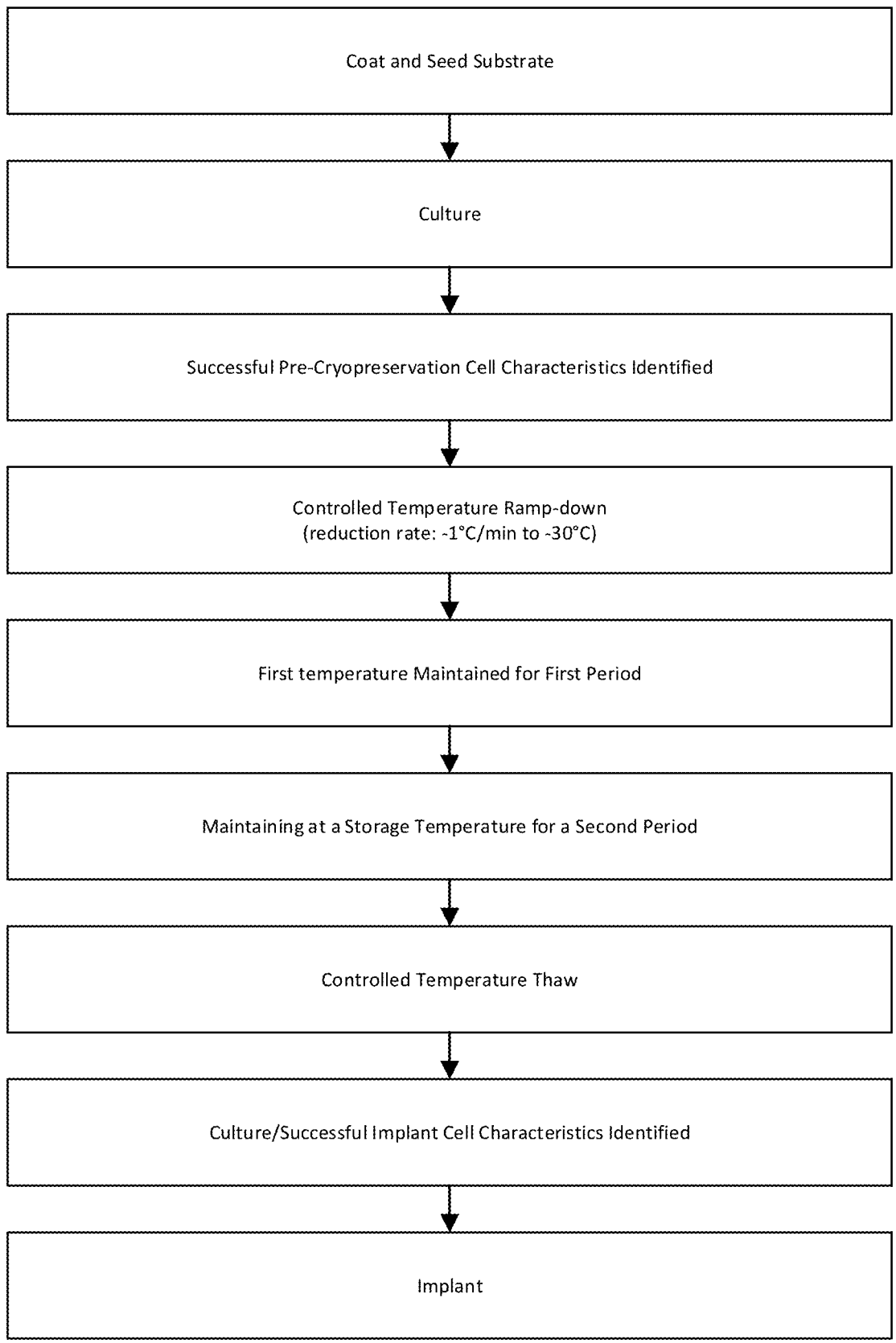
FIG. 1 is a flowchart illustrating the cryopreservation process from substrate preparation to implant in accordance with an embodiment.
Figure 2:
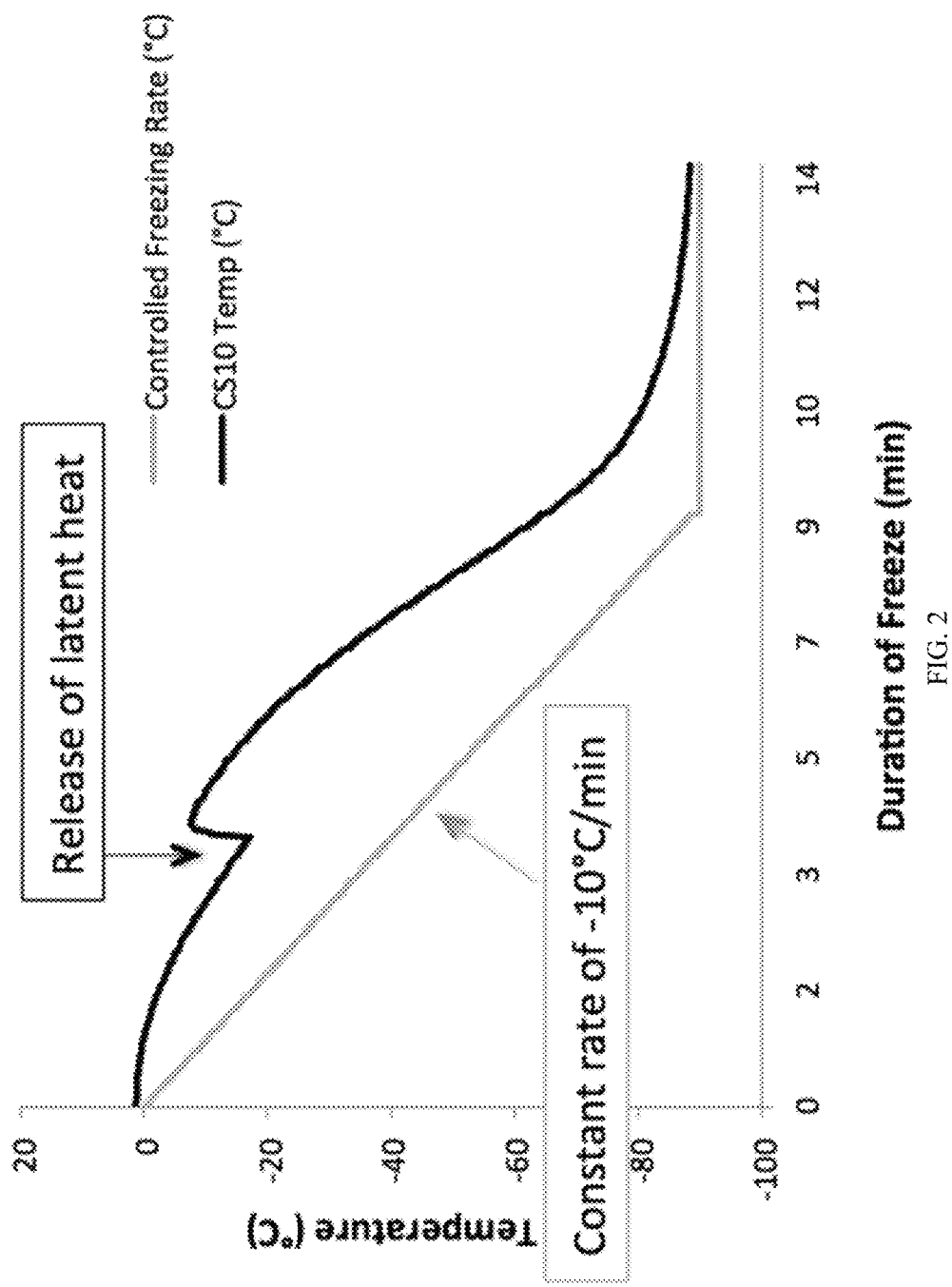
FIG. 2 is graph showing the release of latent heat by the cells seeded on the substrate during a controlled temperature ramp-down step of cryopreservation in accordance with an embodiment.
Figure 3:
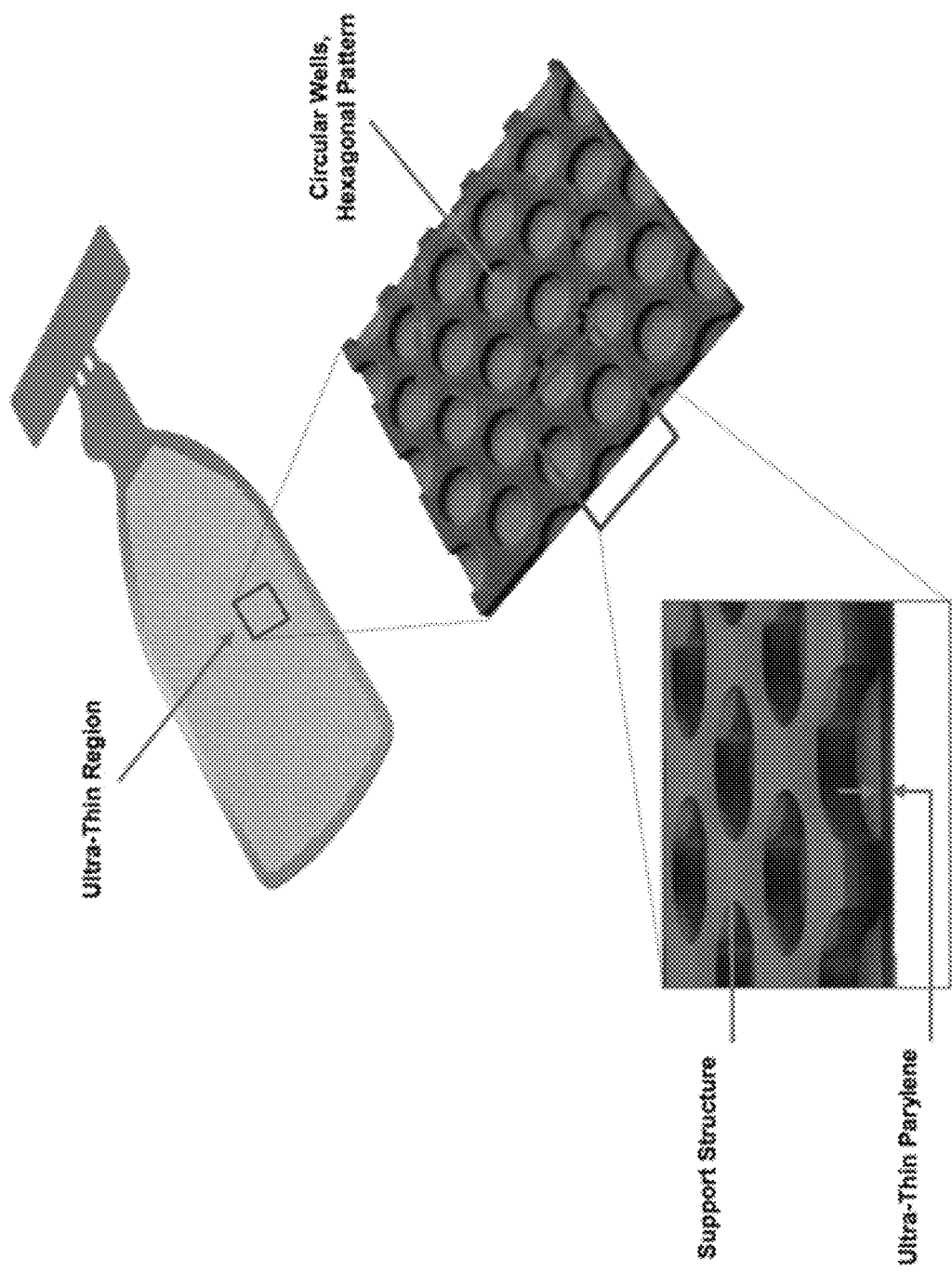
FIG. 3 an example substrate for cell seeding emphasizing the patterned thin surface for nutrient diffusion and support structures to allow for cell growth in accordance with an embodiment.
Figure 4:
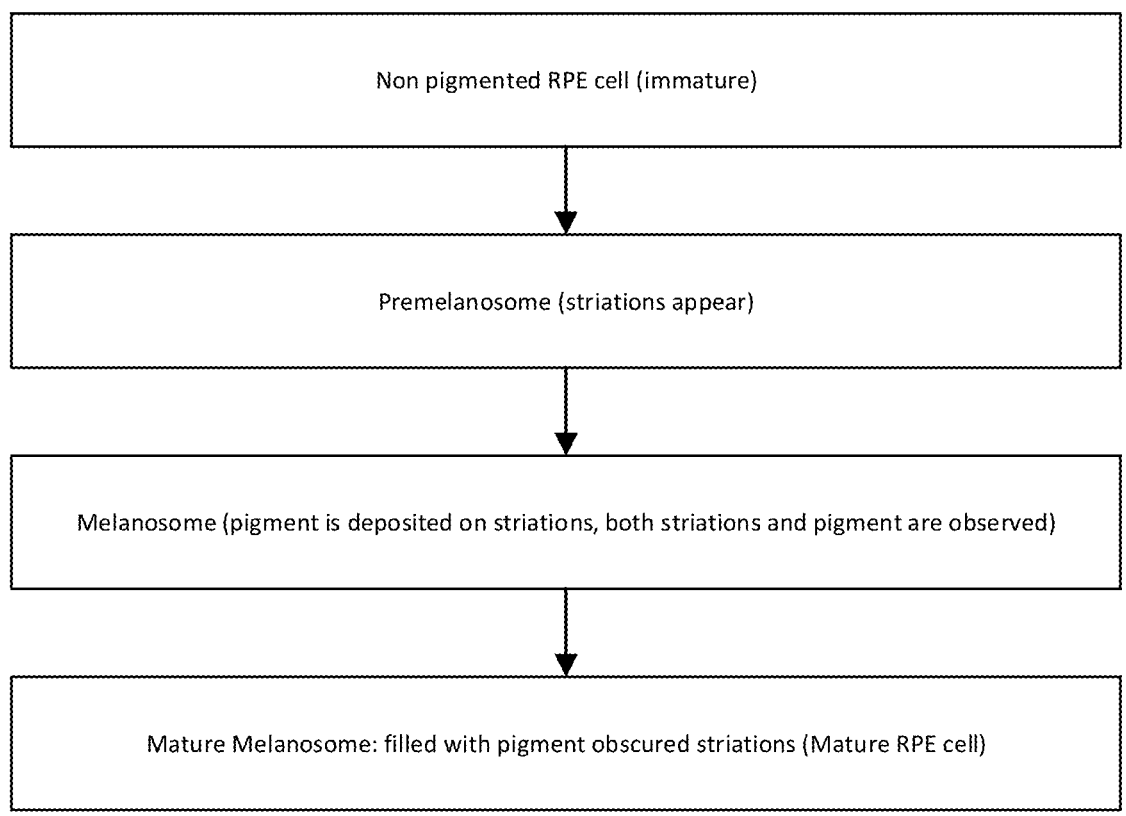
FIG. 4 is a flowchart illustrating the steps of pigmentation for an RPE cell, specifically, (A) Immature non-pigmented RPE cell, (B) Premelanosome (striations appearing), (C) Melanosome (pigment is deposited on striations, both striations and pigments are observed), (D) Mature RPE cell (filled with pigment obscuring striations), in accordance with an embodiment.
Figure 5:
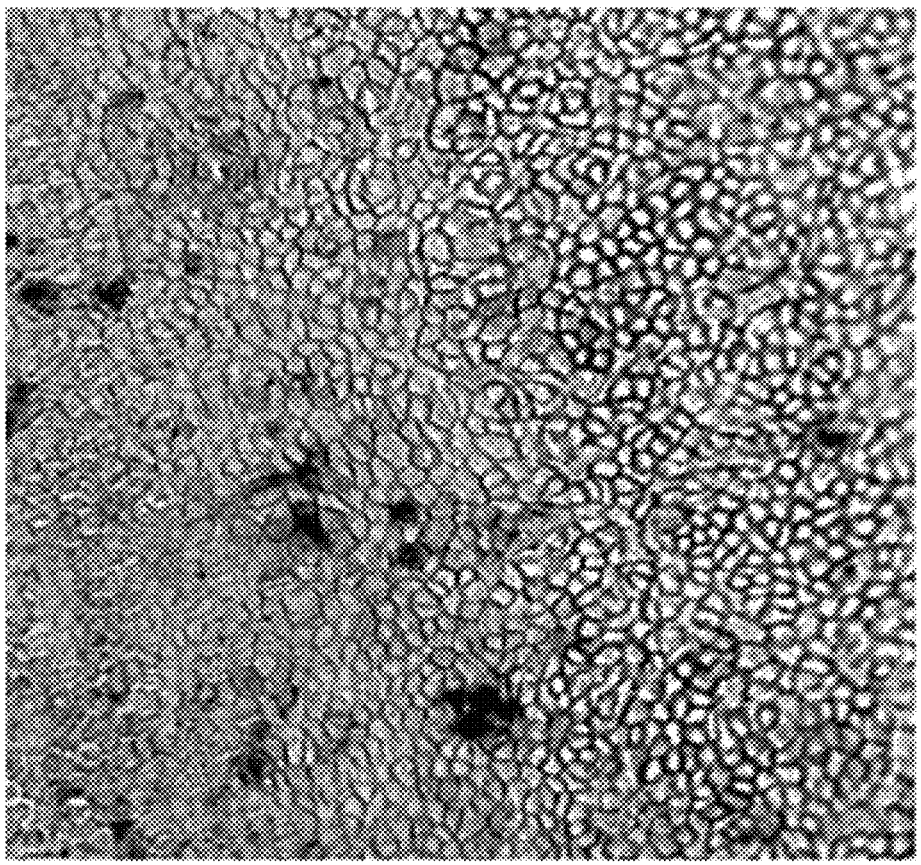
FIG. 5 is a picture of exemplary cuboidal cobblestone morphology.
Figure 6:
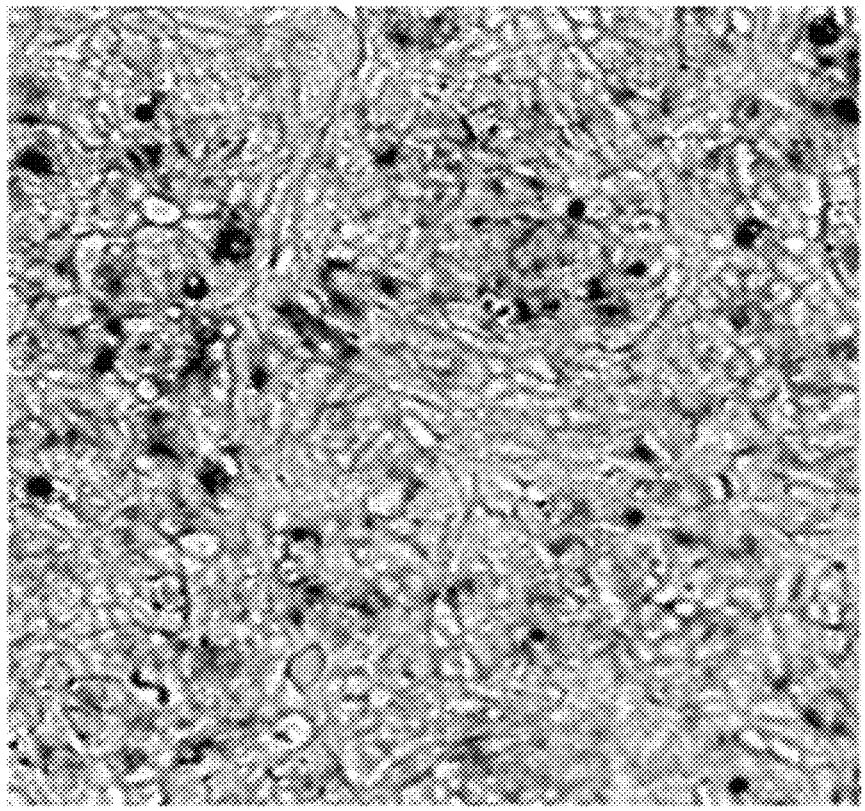
FIG. 6 is a picture of disorganized morphology that contains a mix of cobblestone morphology and fibroblast morphology.
Figure 7:
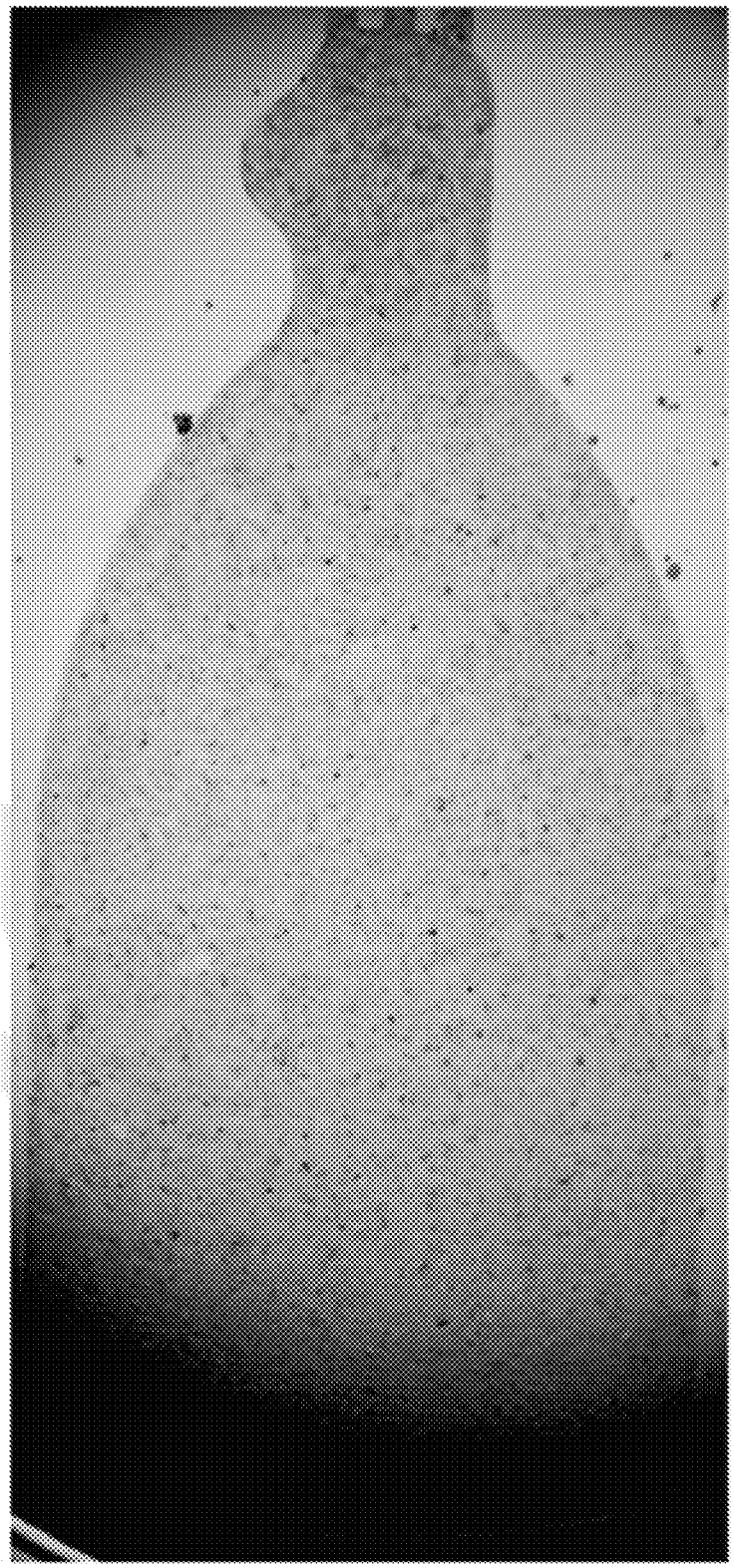
FIG. 7 is a picture of a substrate that has uniform cell growth and is near confluent (90-99% confluency) or 100% confluent in accordance with an embodiment. Indistinguishable by visual observation, and requires imaging technology for actual percentage of confluency.
Figure 8:
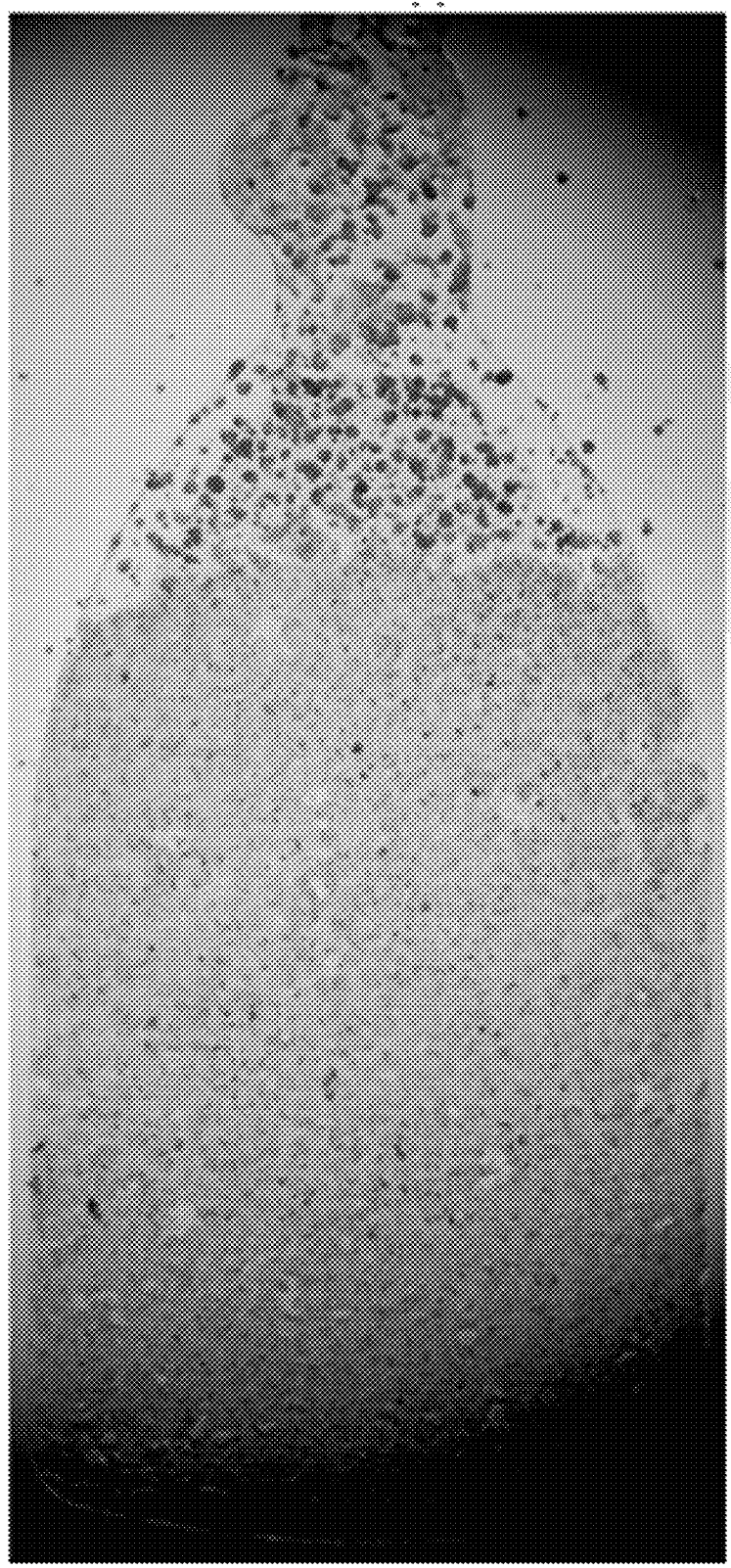
FIG. 8 is a picture of a substrate that has non-uniform cell growth and is only about 70% confluent in accordance with an embodiment.
Figure 9:
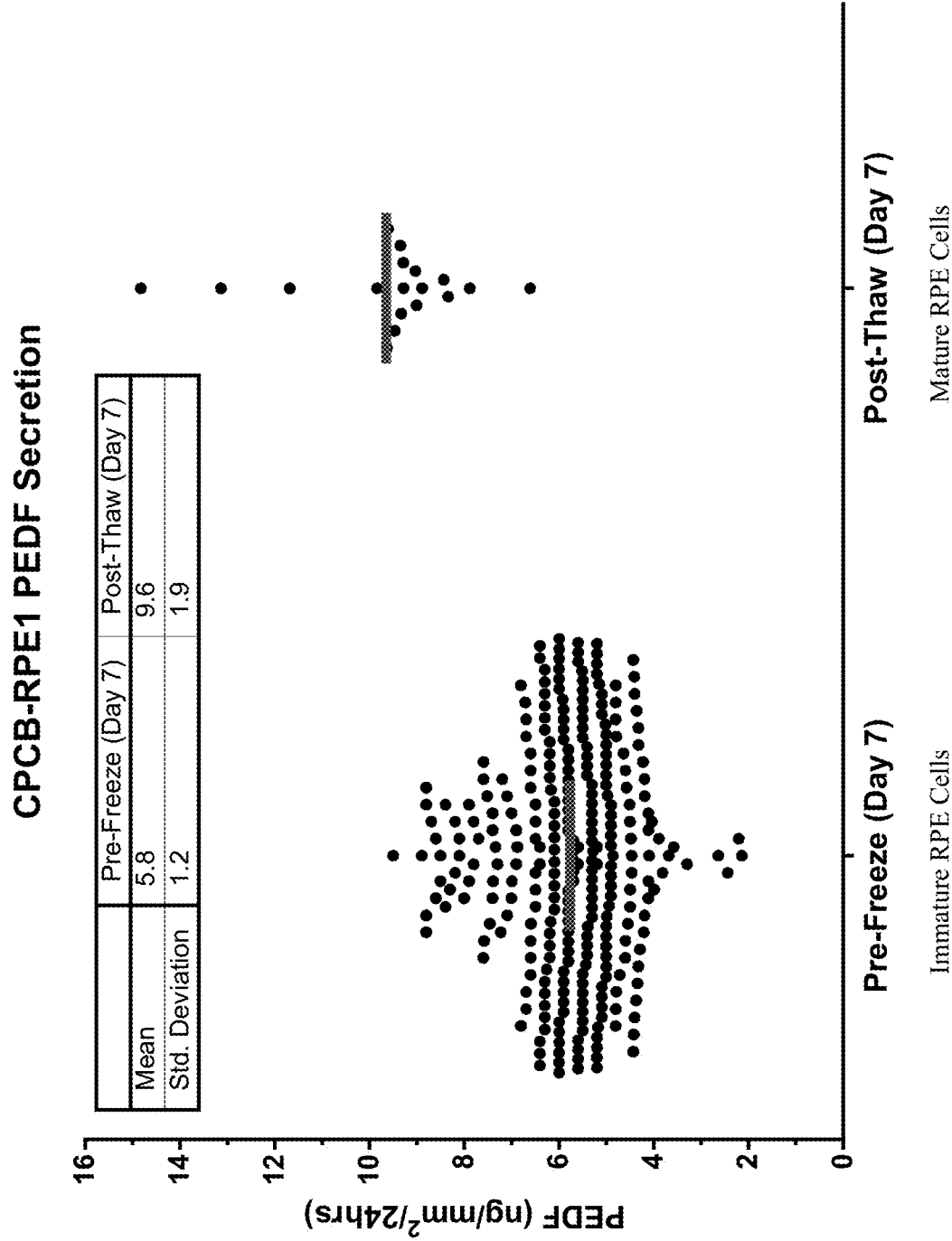
FIG. 9 is a graph illustrating the difference in PEDF secretion by immature RPE cells vs. mature RPE cells in accordance with an embodiment.
Figure 10:
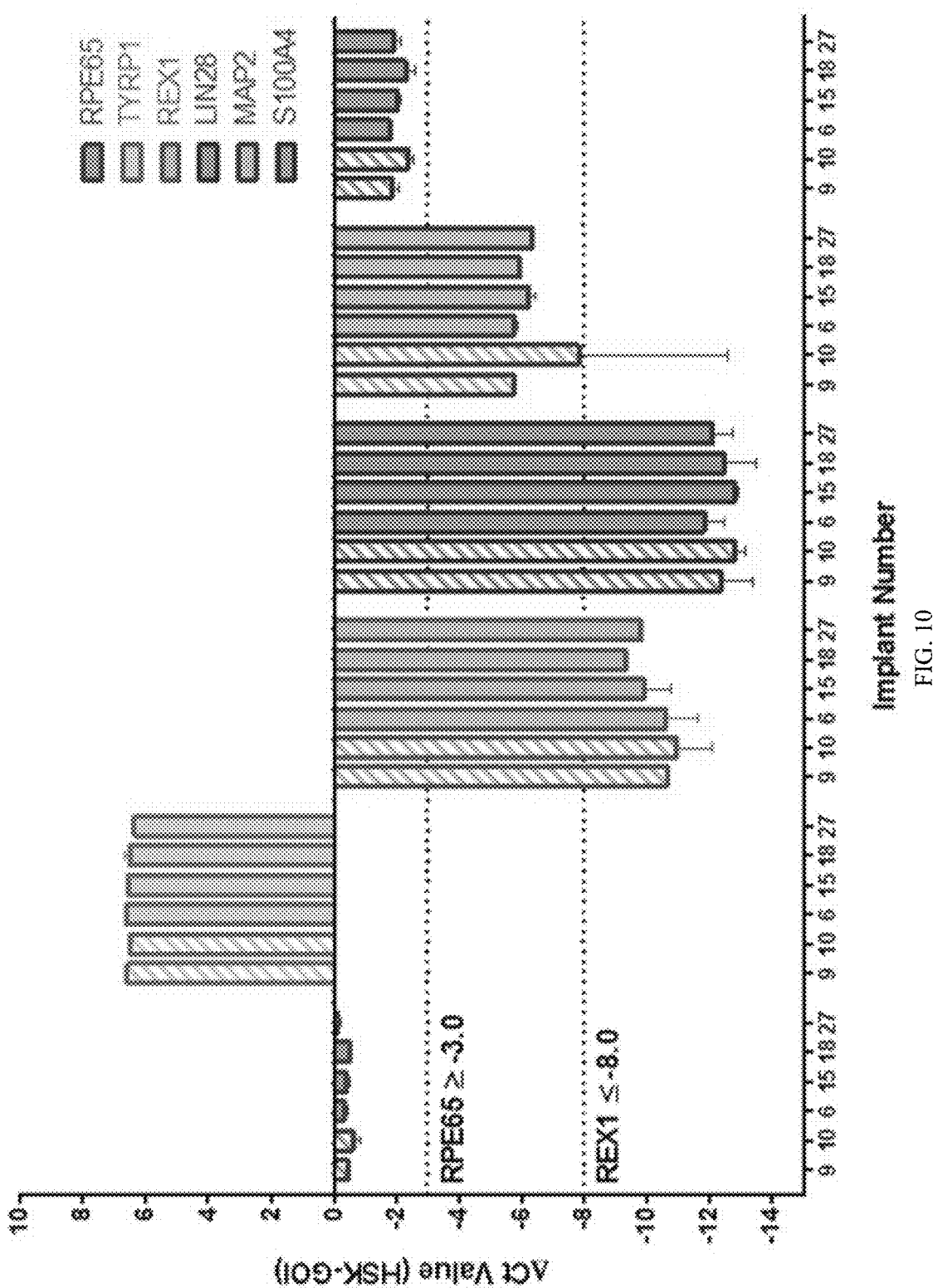
FIG. 10 is a graph illustrating various values of gene expression measured by RT-qPCR in accordance with an embodiment. Specifically, RPE65 ΔCt≥−3.0, REX1 ΔCt≤−8.0 which are ranges of a mature RPE cell. Geometric mean of reference genes (EIF2B2,SERF2,UBE2R2) Ct≤32.0. Several other genes including MAP2, S100A4, TYRP1, and LIN28A are tested for information only.
Figure 11:
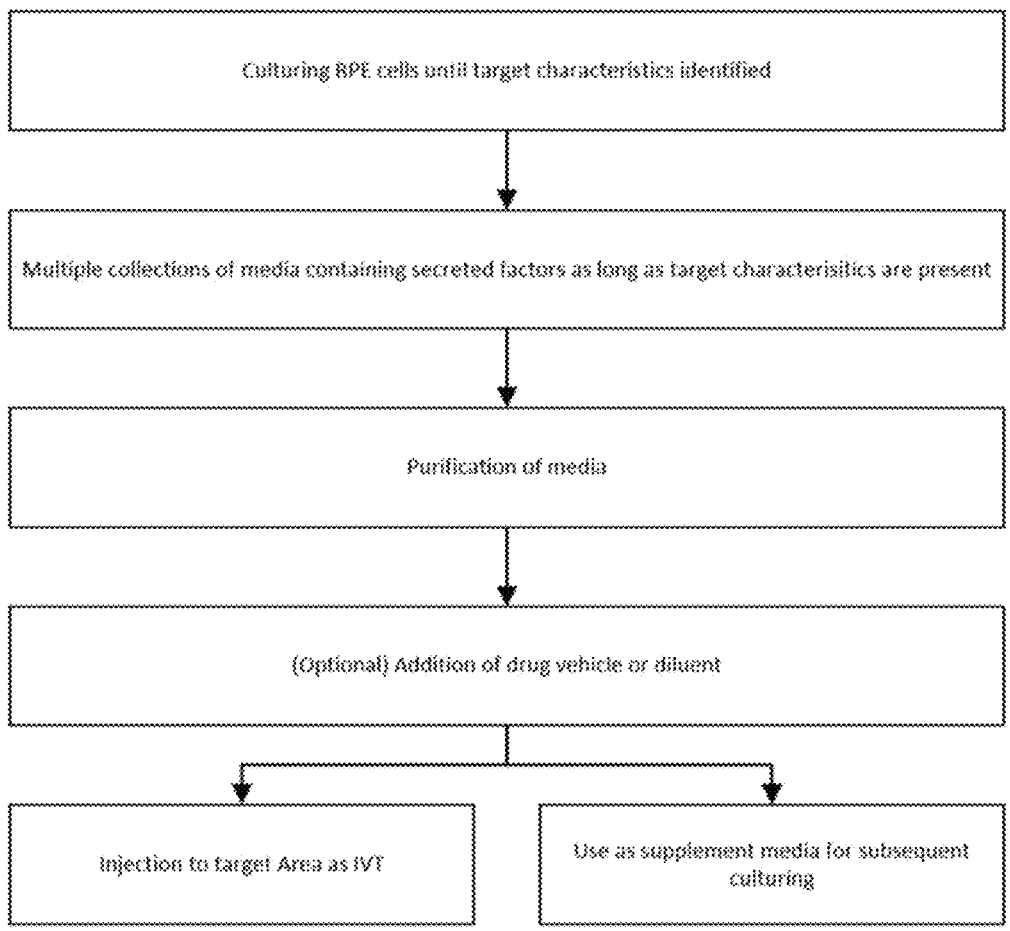
FIG. 11 is a flowchart illustrating the manufacturing steps of a target supernatant containing specific cell secretion factors that may be injected as an IVT or used as supplement media for subsequent culturing in accordance with an embodiment.
Figure 12:
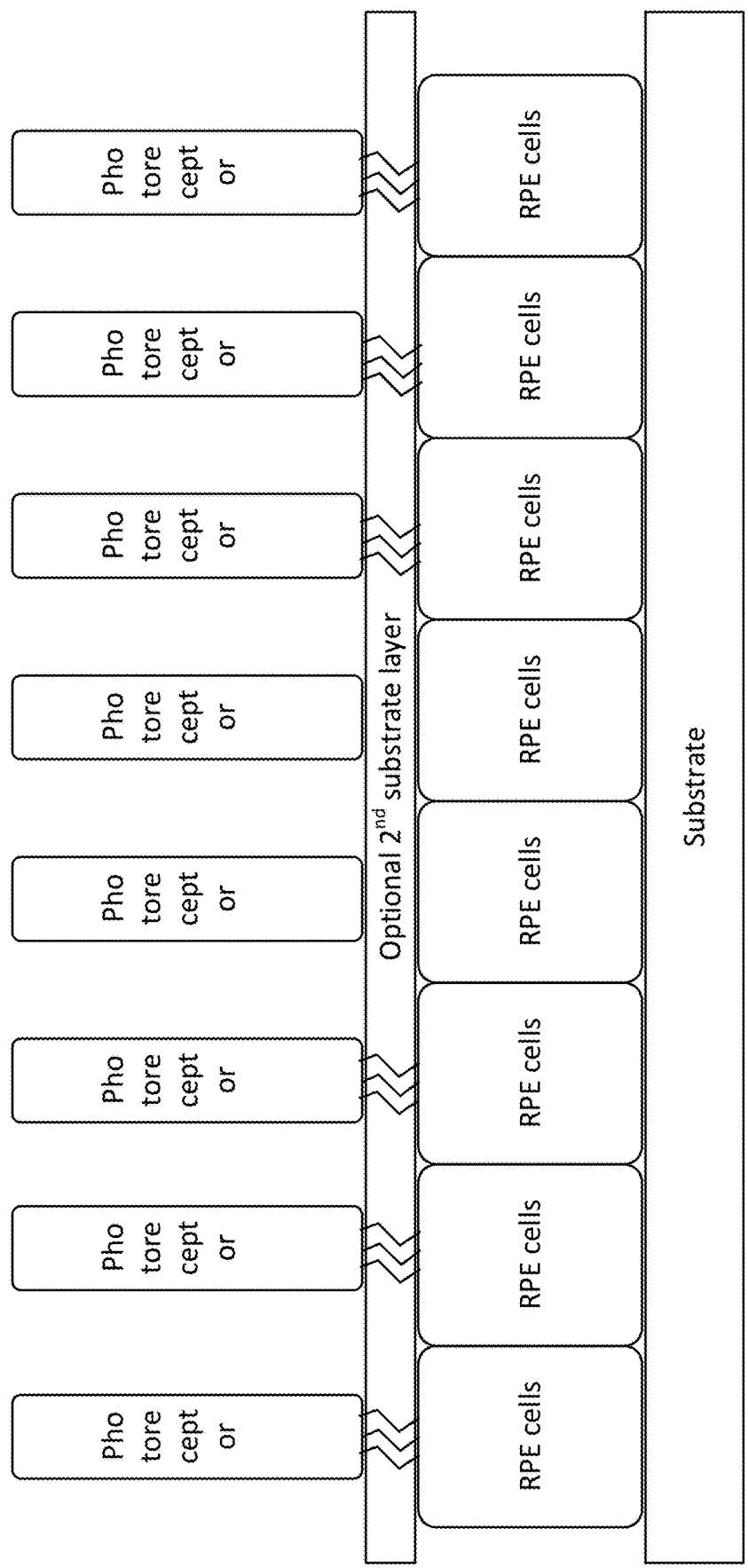
FIG. 12 is a simplified diagram of an embodiment with emphasis on the interaction between photoreceptors and RPE cells on one or more substrates.
Figure 13:
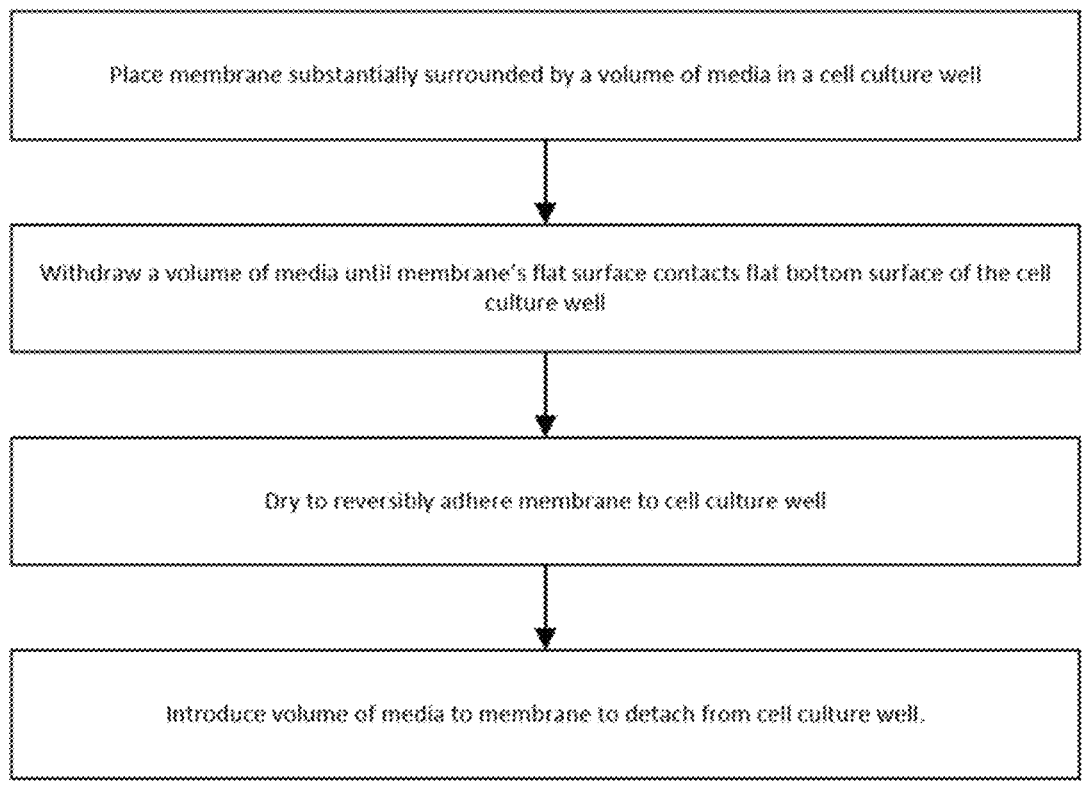
FIG. 13 is a flow chart illustrating the process of reversibly adhering a membrane to a cell culture well in accordance with an embodiment. Such method is beneficial for securing the substrate for automated substrate coating or cell seeding processes that rely about secure X and Y axis orientation. The adhesion is reversible by introducing a volume of media to the membrane.
Figure 14:
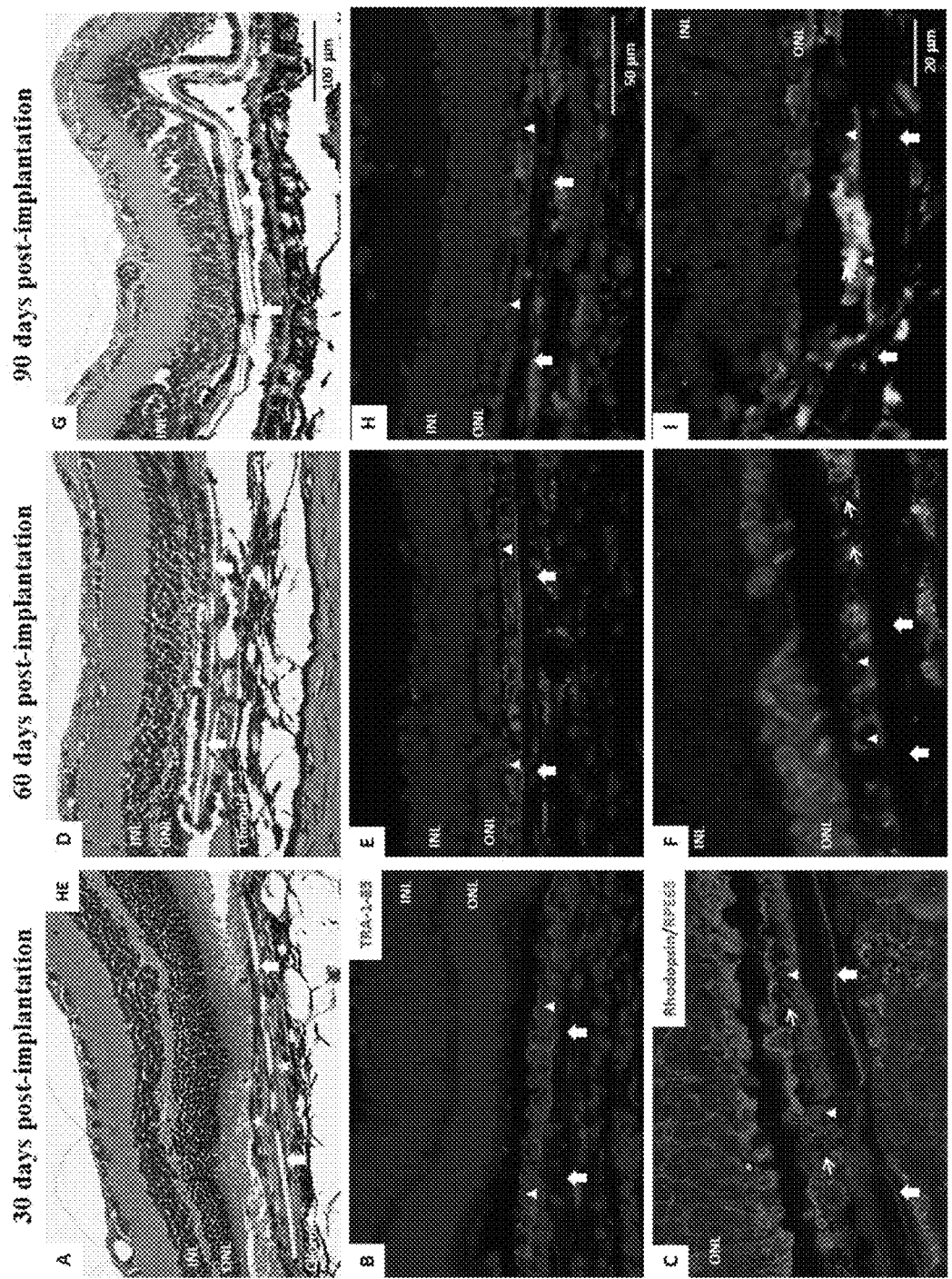
FIG. 14 illustrates various contrast images comparing overall cell viability post-cryopreservation and post-implantation along with certain gene expressions highlighted in accordance with an embodiment.
Figure 15:
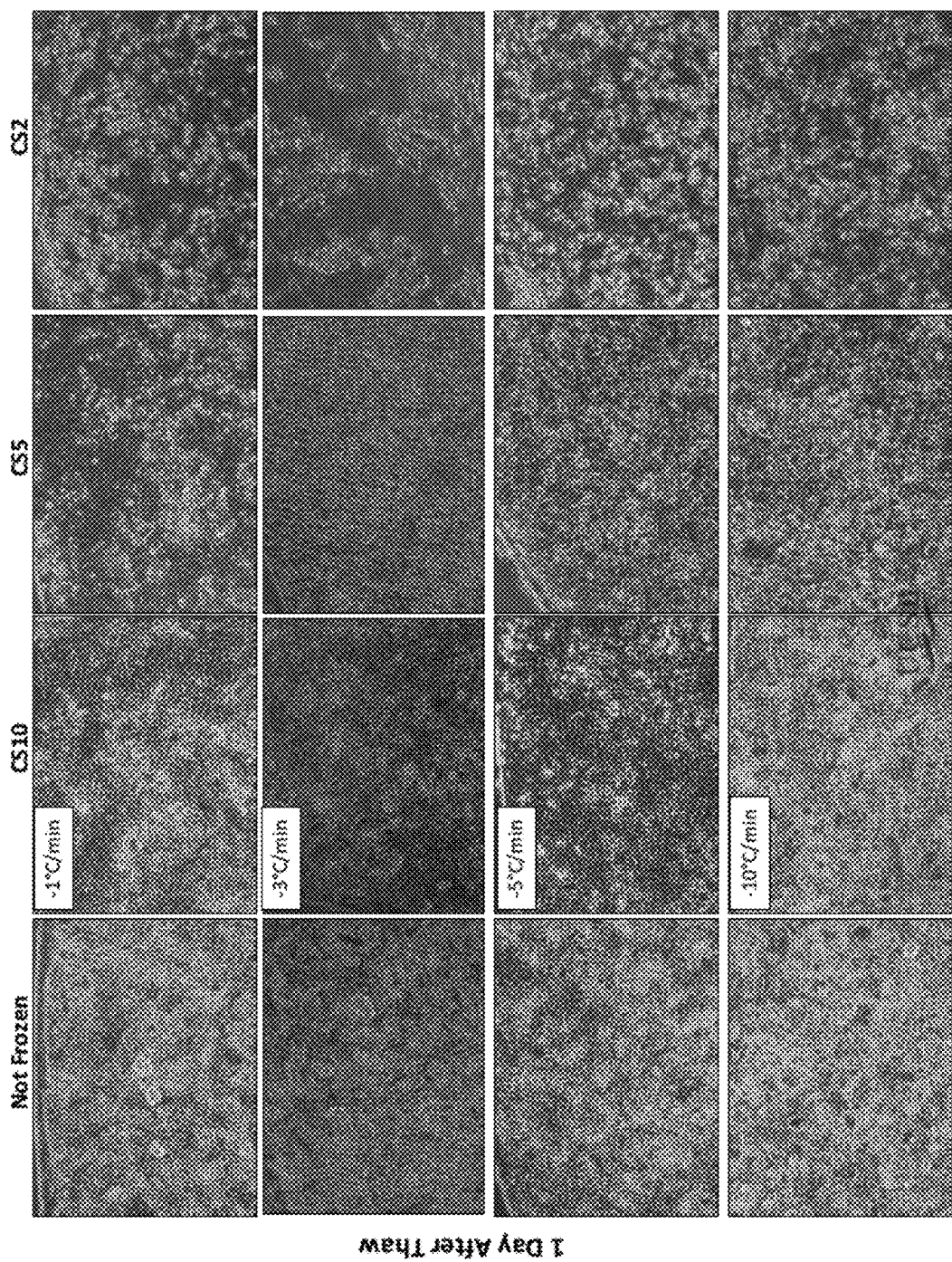
FIG. 15 illustrates multiple images showing the difference in cell morphology 1 day after thaw due to difference in cryo-protectant used in accordance with an embodiment as compared to a control of non-frozen cells.
Figure 16:
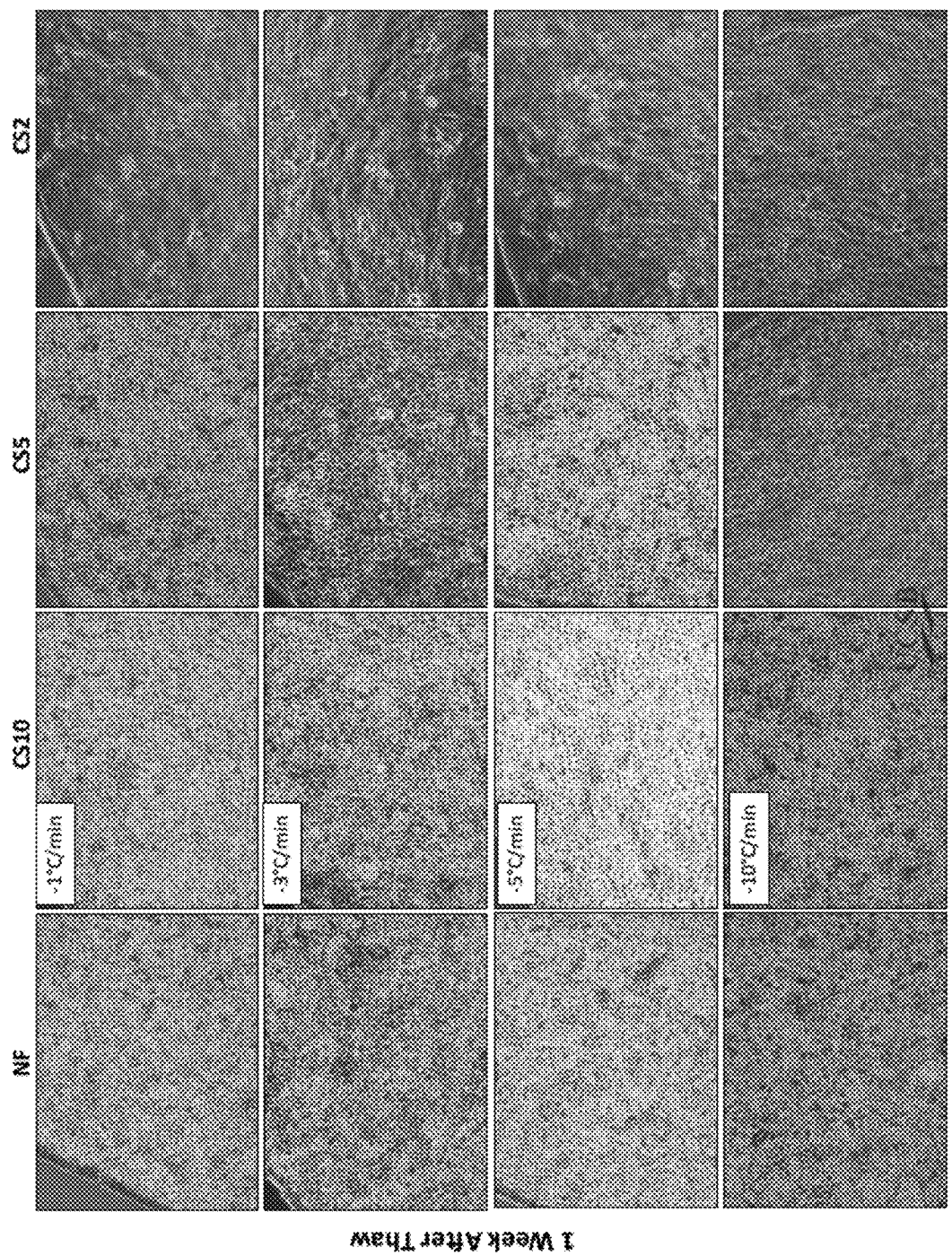
FIG. 16 illustrates multiple images showing the difference in cell morphology 1 week after thaw due to difference in cryo-protectant used in accordance with an embodiment as compared to a control of non-frozen cells.
Figure 17:
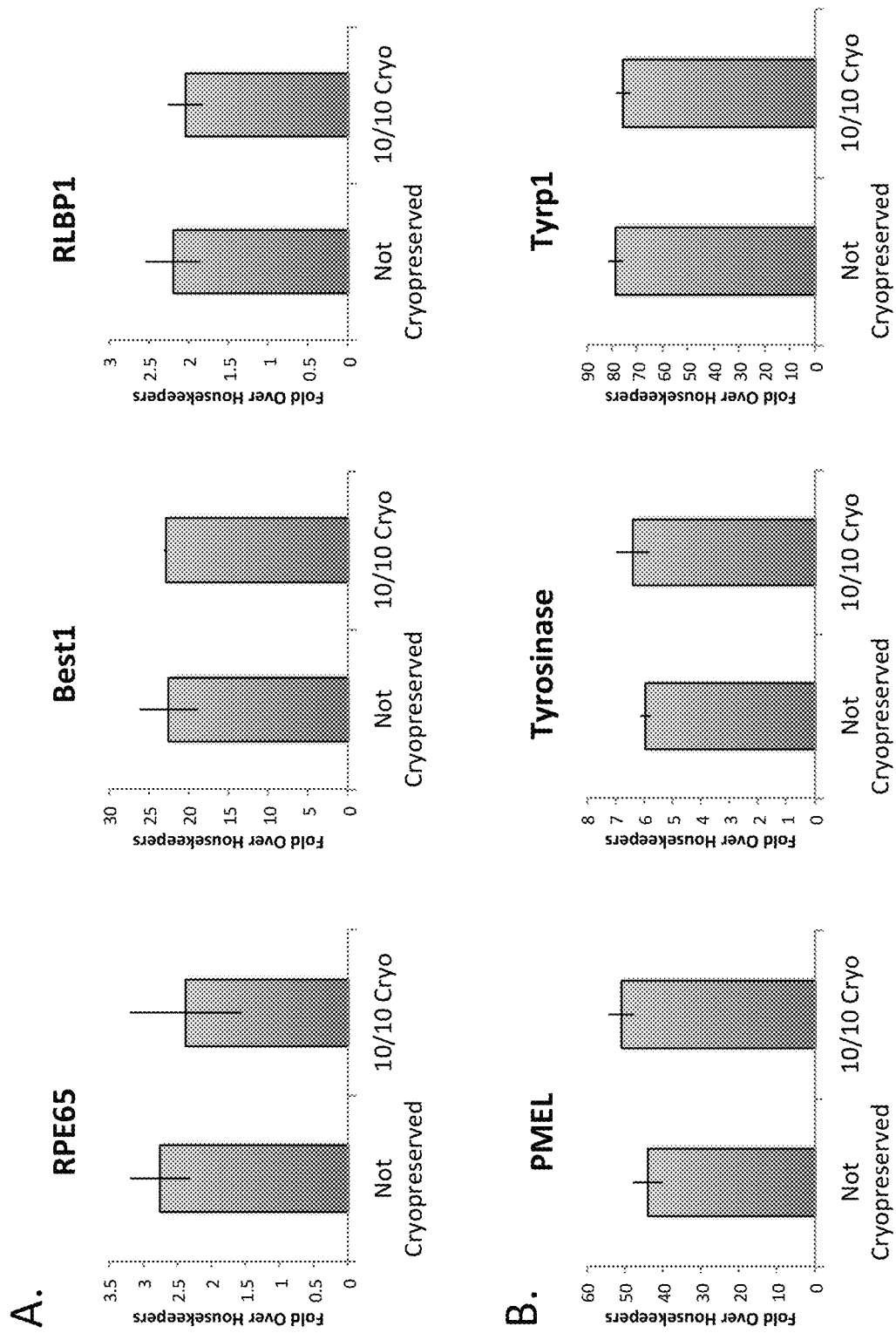
FIG. 17 shows six graphs of gene expression obtained from a single sample comparing non-cryopreserved and post-cryopreservation in accordance with an embodiment.
Figure 18:
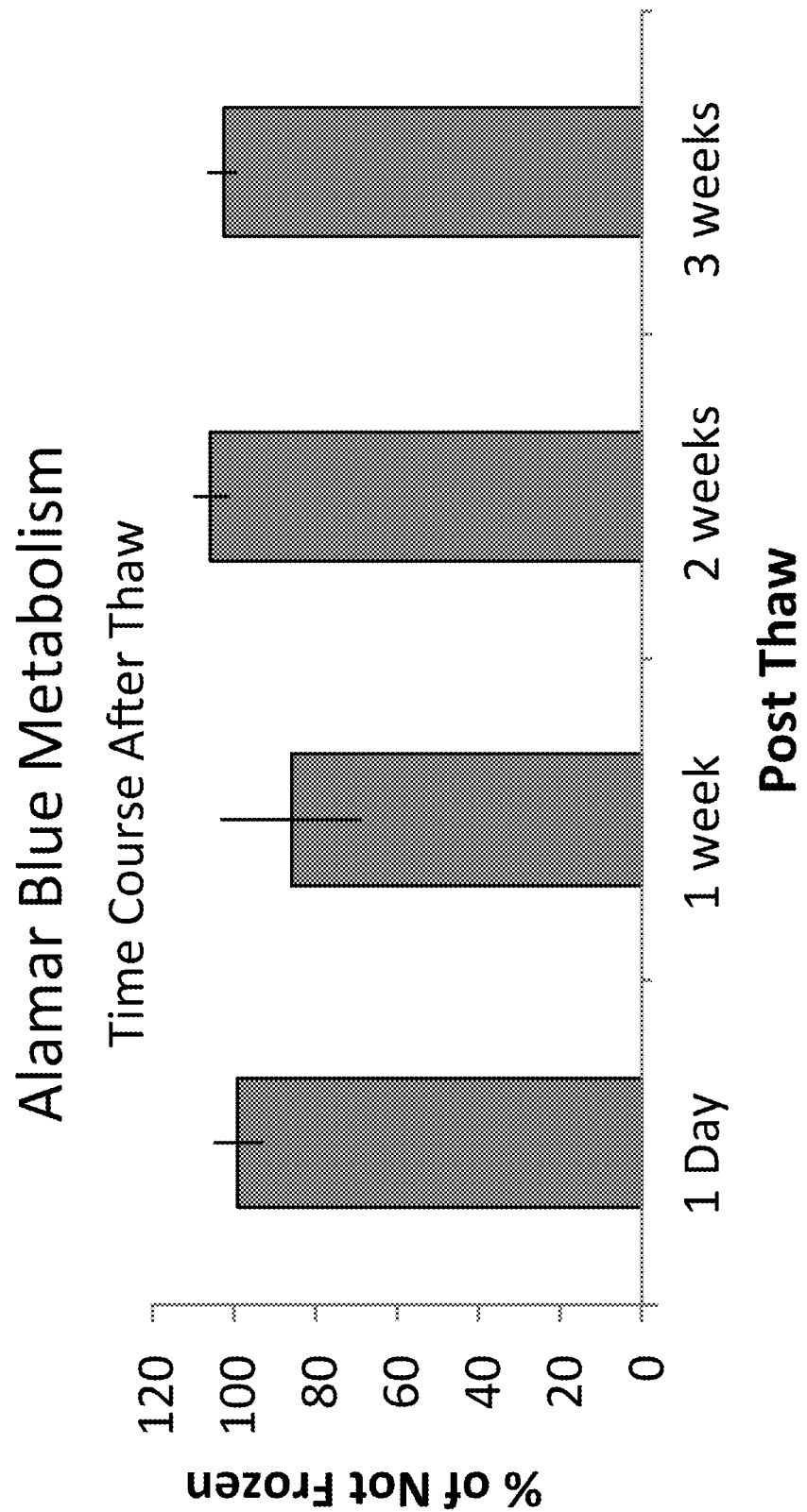
FIG. 18 show a graph of metabolism per colormetric metabolism assay in accordance with an embodiment.

The present invention relates to, generally, cell seeded substrates, cell evaluation processes, and methods to increase viability of the cell seeded membranes through the seeding onto substrate and cryopreservation process. Cell seeded membranes, unlike conventional single cell or cluster of cells, require special considerations for increasing viability post-cryopreservation and thaw. By specifically making the below mentioned adaptations, results have shown not only increased cell survivability but increased health (e.g. metabolic activity, longevity) of the surviving cells including post-implantation.

Cryopreservation Optimization: Substrates/Membranes

In several embodiments, the substrate comprises a biocompatible polymer to act as a seeding surface. In several embodiments, the substrate comprises parylene in combination with other materials, the other materials being either biodegradable or non-biodegradable. In several embodiments, the substrate is treated such that it has one or more characteristics that enhance viability of the seeded cells. For example, in several embodiments, the substrate further comprises a coating to enhance adhesion of the cells to the substrate. In some embodiments, the coating comprises one or more of Matrigel, vitronectin, fibronectin, and retronectin, or layer of derivitized parylene. Other cell media and various combinations thereof that are known to those skilled in the art may be substituted. Other coatings or surface modifications are used in other embodiments, in order to achieve improved cell adhesion to the substrate and/or improve the durability and/or viability of the cells and the substrate during and after the cryopreservation process. For example, in several embodiments, the coating enhances the viability of the cells during cryopreservation, after cryopreservation, or both. In another example, the cell growth surface of the substrate is treated with oxygen to create a hydrophilic cell growth surface. Other surface treatments include, oxygen plasma treatment, chemical etching, and additional polymer deposition. Additional polymer deposition is especially useful when different parylene types are used based on their functional needs such as Parylene-C for its elasticity (e.g. elongation to break (%) of 200), Parylene-N for its high oxygen gas permeability (cc.mm/m$^2$ day). (Specialty Coating Systems, A KISCO Company). Furthermore, functionalized parylene can be deposited onto surfaces to confer active chemical functionalities including but not limited to: (1) R-hirudin, a protein with anticoagulant properties, thereby increasing implant haemocompatibility, (2)amine functional groups to covalently link fibronectin to the surface for improving osteoblast cell adhesion, and (3) pNIPAM chains to form a hydrophobic surface that promotes tissue adhesion (Tan et al. 2010).

In some embodiments, the characteristics of the substrate comprise one or more of the coefficient of thermal expansion of the substrate, a substrate elasticity parameter, or a substrate thickness. In several embodiments, the substrate comprises parylene and is selectively permeable and the characteristic comprises substrate thickness, and the thickness is selected to allow nutrients to pass through the substrate. The substrate may have no through holes and rely solely on the thickness of the substrate for permeability characteristics. Thus, upon thawing and subsequent implantation at a target site, the substrate permits adequate nutrient passage to the cells and/or adequate passage of cellular waste material away from the substrate. In some embodiments, the thickness is selected to yield a thermal coefficient of expansion of the substrate such that it has reduced adverse impact on the seeded cells. The thickness is specifically important in embodiments where the cells to be cryopreserved are seeded in between two or more materials (e.g. a sandwiched, entrenched, or other embodiments) wherein expansion of the cell or the cryo-protectant used may expand during freezing, thereby causing shear, torsional, or other stresses that would damage the substrate and/or cells. In some embodiments, the material and thickness are selected to have thermal energy release characteristics that do not interfere with the release of latent heat of the seeded cells. In some embodiments, the material configuration is selected to have increased sheer force resistance such as a hexagonal, honeycomb pattern of a support structure as may be encountered during cryopreservation and thawing procedures.

In some embodiments where two or more layers of differing cells are placed on the membrane, a second substrate layer may be placed in between such cell layers to promote segregated proliferation within separate layers. For example, when the cell seeded substrate consists of the specific order of a first substrate layer, first layer of cells consisting of RPE cells with a basal side interfacing with the substrate, a second layer of cells consisting of photoreceptor cells interfacing with the apical surface of the first layer of cells, a second substrate layer may be placed in between the first and second layers of cells. In one embodiment, the two cell layers are grown on the first substrate layer simultaneously, with the first cell layer of RPE cells being seeded onto the substrate first and the second cell layer of photoreceptors being seeded onto the substrate on top of the RPE cells at a subsequent time. Such time may be 1-10 days later, thereby allowing RPE cells to primarily adhere to the substrate first. In other embodiments, retinal precursor cells, epithelial cells, other ophthalmic cells, stem cells, or reprogrammed cells that will differentiate into another cell type may consist of one or more of the layers. Further embodiments may include, certain engineered cells by gene editing to specifically produce certain factors (e.g. proteins, growth factors, antibodies) to promote specific cell signaling to reprogram an adjacent layer. In various embodiments, RPE stem cells may be modified to secrete neurotrophic factors (e.g. PEDF, CNTF, BDNF) that further support survival of photoreceptor cells. In further embodiments, over expression of surface integrins enhances RPE adhesion to the Bruch's Membrane, increase in melanin to lower risk for AMD, and over expression of receptors required for phagocytosis increases clearance of lipofuscin and other metabolic waste products that may hinder cell layer health.

In other embodiments, each cell layer is grown independently on separate substrates. In this embodiment, it may be beneficial to have the second substrate be biodegradable or consist of growth media in a gelatinous state that will dissolve or be degraded and/or absorbed by one or more adjacent cell layers after stacking and implantation. The growth media may consist of specific growth factors (e.g. bovine serum albumin (BSA), Activin A, fibroblast growth factor (FGF), insulin-like growth factor (IGF1), human dickkopf WNT signaling pathway inhibitor (DKK1), and noggin)) or antibodies (complementary to functionalized groups embedded in the substrate of parylene as described below) to improve the attachment of one or more layers.

Controlling nucleation, the onset of change of state from liquid to crystalline, and the temperature compensation provided during controlled rate preservation for release of latent heat (Exhibit X) are known to improve post-cryopreservation and thawing cell viability. In many embodiments, the substrate is oriented parallel to the seeded cells due to the configuration and seeding area of the substrate. Therefore, the substrate is in intimate contact and/or close proximity to all of the seeded cells, thereby allowing for a homogenous nucleation of all cells simultaneously and efficient temperature compensation in response to the latent heat release of the seeded cells. This is an especially beneficial factor for embodiments in which the seeded cells grow into a near-confluent (e.g. >98%) or confluent monolayer. Thereby, during the cryopreservation process, the substrate efficiently induces nucleation without requiring other methods known in the art including: seeding ice crystals or other nucleating agents, mechanical vibration, electrofreezing, etc. which would negatively affect the uniform cell layer formed on the substrate. Certain methods of nucleation above may be used in conjunction with the substrate which only aides in the nucleation process as the cells are in a confluent or near-confluent orientation. The substrate configuration and spatial relation to the cells thereby additionally contribute beneficially to the viability of cryopreserved cells in addition to the temperature compensation provided by controlled rate freezing during the process of latent heat release by the seeded cells. The latent heat release is partially dependent on cell lines, but primarily dependent upon the composition of the cryopreservation media used. In otherwords, the substrate surface being substantially parallel to the monolayer of cells seeded on the substrate, effectively acts as a heat sink to efficiently heat transfer at the time of cryopreservation and thawing including at the time of latent heat release from the seeded cells.

Ideal substrates may also have beneficial characteristics such as those seen in the substrate described in U.S. Pat. No. 8,808,687. Substrate characteristics include: a cell growth surface to promote adhesion and the generation of a monolayer of cells, a perimeter that prohibits cell growth (e.g. perimeter portion of the substrate does not consist of a thinned membrane portion for sufficient nutrient and waste transport for cell growth affinity, and/or the perimeter consists of a raised lip, etc.), and allows for mechanical manipulation and implantation adjacent to a target tissue.

In certain embodiments, the substrate is designed to have an optimal non-planar normal state that conforms to the desired implantation site. Although the substrate may be manipulated during culture and cryopreservation to maintain a planar shape for easier handling, ease of cell-seeding by automation machines, and improved cell viability, it may be beneficial to be in a non-planar shape once implanted. In embodiments where the cell seeded substrates contain RPE cells and are implanted to adequately cover geographic atrophy areas within the retina, the substrate is optimally curved to match the radial curvature of the retina within the eye. The curvature induces parallel growth of the external limiting membrane (ELM) which is indicative of restoration of photoreceptor microstructures and adjacent visual functionality. The substrate-parallel formed RPE monolayer and photoreceptors serve as an adherent for precursor cells, which upon maturation form the ELM. Comparatively, RPE cell injections of standalone cells, non-distinct shape cellular gels and suspensions have shown poor clinical outcomes.

Method of Reversibly Adhering Substrate/Membrane onto Tissue Culture Vessel

In embodiments in which a small substrate/membrane (less than 100 mm$^2$), or thin substrate/membrane (less than 50 microns), is a requirement due to later implantation, it is difficult to maintain the substrate within a standard culture well as the minimal mass makes it buoyant within a volume of media, thereby allowing a substrate to move about, possibly dislodging seeded cells. One method to prevent such movement of substrates is to reversibly adhere the membranes to the tissue culture plate by evaporative drying. This may seem counter intuitive as many cell culture plates have additional features to minimize evaporation (e.g. an evaporation moat to be filled with sterile water or media in ThermoFisher Scientific Nunc Edge 2.0 96-well cell culture plate). In one embodiment, the membrane is first placed in a well of the tissue culture plate with a solution to be evaporated (e.g. Dulbecco's Phosphate Buffered Saline (DPBS). The DPBS is slowly withdrawn from the well until the membrane is flat on the bottom of the well with a residual amount of liquid left between the membrane bottom and the well bottom surface. Once repeated in all other applicable wells, the tissue culture plate is dried. Various methods of drying include use of a desiccator, temperature/humidity controlled chamber, baking in a drying oven, or leaving in a controlled room such as a clean room. During this drying phase, the residual DPBS evaporates, thereby adhering the membrane to the bottom of the well, thereby making it easier to apply a cell growth coating (e.g. vitronectin) as well as cell seeding. By limiting movement within the well, automated cell seeding machines may be used for uniform seeding which requires known X, Y, and Z axis and is usually limited to two dimensional function. After cell seeding, the membrane is reversibly adhered by introducing DPBS into the well allowing the membrane to dislodge from the well bottom surface, and movable to another well for culturing. In other embodiments, various other solutions that do not negatively alter pH, salinity, or other cell growth factors may be used instead of DPBS.

Cryopreservation Optimization: Cell Biological Evaluation

In embodiments of cryopreserving cells seeded on a substrate, optimal cryopreservation viability characteristics are different at each manufacturing stage.

First, at the time of cell seeding defined as Day 0, the cells are optimally selected to be non-mature cells that more easily adapt to the seeding process and maintain viability post seeding. In the embodiment of RPE cells, these characteristics include: (non-polarized or partially polarized, (ii) minimal to light pigmentation or absence of melanin, (iii) seeding at seeding densities that are <100% confluent (e.g. between 50-90% confluent, and more ideally 70-80% confluent).

In embodiments of cryopreserving RPE cells seeded on a substrate, the RPE cells are selected and cryopreserved when representing optimal cryopreservation viability characteristics post-seeding. Such characteristics are observed between 2 to 10 days after seeding, and in most embodiments between 6 to 8 days after seeding. Optimal cryopreservation viability characteristics observed immediately prior to cryopreservation include: (i) non-pigmented or minimally pigmented RPE cells (including depigmented RPE cells, RPE cells with altered pigmentation caused by natural or induced genetic mutations in the pigmentation pathway or chemical induction of altered pigmentation or a combination thereof), (ii) non-polarized or partially polarized RPE cells, (iii) RPE cells with over 50% mature cobblestone morphology, although some fibroblastic morphology may be acceptable (iv) RPE cells with gene expression levels below that of mature cells or lacking specific gene expression, and (v) RPE cells in a subconfluent (less than 100% or subconfluent (greater than 90% confluence) monolayer configuration exemplifying positive attachment and growth on the substrate as well as formation of tight junctions, a characteristic of an epithelium layer.

One characteristic of optimal cryopreservation viability RPE cells is non-pigmentation or minimal/partial pigmentation. RPE cells contain numerous melanosomes, pigment granules that extend from the apical area into the middle portion of the cell. Certain RPE cells such as those interfacing with the macular area are more densely pigmented. Non-pigmented or limited pigmentation RPE cells can be non-fully differentiated, non-isolated, and/or non-purified cells. Various methods may be implemented including depigmenting RPE cells by chemical removal (e.g. melanogenesis inhibitors), alteration of growth media, interaction with physiologically adjacent cell types etc. In one embodiment, the melanogenesis inhibitor, propylthiouracil (PTU) is used to prevent the multi-step conversion of Tyrosine into dopaquinone, and Eumelanin. Such methods of inhibiting melanogenesis and the absence of melanin at the time of cryopreservation promote RPE cell survival post-thaw. PTU may be substituted by various other substances known in the art to prevent or limit melanogenesis related pathways.

Another characteristic of optimal cryopreservation viability RPE cells is nonpolarization, partial polarization, or full polarization. RPE cells that are polarized distinguish between the apical (corresponding to the retinal facing side of the RPE cells) and basal (corresponding to the choroidal facing side of the RPE cells) directions that mimic the physiological characteristics including: apical microvilli, well-defined tight junctions, membrane transport capability and melanocytic pigmentation. The polarization may be visually distinguished or be distinguished by the measured ratio of apical, basal, and non-polar dependent cell secretions.

Yet another characteristic of optimal cryopreservation viability RPE cells is the observance of a cobblestone morphology. RPE cells of a differentiated, isolated, and/or purified cells take on an appearance of cuboidal cobblestone morphology.

An additional characteristic of optimal cryopreservation viability RPE cells is gene expression levels below that of mature cells or lacking specific gene expression. This characteristic may be tested for by RNA or other nucleic acid expression, protein expression, lipid expression, glycosylation pattern, immunohistological staining, or electrophysiological properties. Secondary measurement techniques such as measurement of secretome levels may also be alternatively or additionally implemented.

Another characteristic of optimal cryopreservation viability RPE cells is a subconfluent monolayer configuration. Confluence is achieved when cells fully grow into all available portions and reach contact inhibition. After reaching confluency, many cell types including mammalian cell types exhibit different characteristics compared to subconfluency. The ideal cell seeding density of monolayer RPE cells on a substrate is between $2.0 \times 10E5$ and $-7.0 \times 10E5$ cells per milliliter of cell suspension, or between $1.0 \times 10E3$ and $4.0 \times 10E3$ cells per square centimeter of substrate surface, or between $1.0 \times 10E5$ and $3.5 \times 10E5$ cells per well of a standard 48-well cell culture plate. Once confluence is reached the cell seeding density is closer to $1.0 \times 10E6$ as is understood from standard characteristic growth pattern of cultured cells that follow a log phase growth as cells proliferate. Cell density can be measured by image analysis, spectrophotometry, electrical/impedance analysis along with other more invasive/destructive processes. A monolayer, compared to a multi-cell layer is promoted by a flat cell seeding surface of the substrate, and matching the substrate nutrient/waste transport ratio to support a monolayer.

Optimal cryopreservation viability RPE cells are achieved between 3-10 days post-seeding of the RPE cells on the substrate where the cells have not reached 100% confluence and fully differentiated on the substrate. The optimal cryopreservation viability RPE cells are obtained during this time window, but may vary according to the cell line used, growth media, substrate characteristics, culture conditions, and combinations thereof. Therefore, one or more of the optimal cryopreservation viability RPE cell characteristics described above should be reviewed both qualitatively and quantitatively prior to the cryopreservation of the cell seeded substrate.

The above mentioned substrate and cell line characteristics should be taken into account to create optimal cryopreservation and thawing protocols to maximize cell viability and functionality and substrate integrity.

Various methods may be used to increase the viability of cells post-cryopreservation thaw including various combinations of cryoprotectants and removal thereof.

Optimal post thaw RPE cells should maintain near 100% confluence, less than 30% dead cells (optimally less than 10%), and maintain the cobblestone morphology. By 5-10 days post-thaw, secretions levels of PEDF is ideally between 5-12 ng/mm2/24 hr and optimally approximately 9.6 $ng/mm^2/24$ hr. In some embodiments, further gene expression testing is completed by quantitative reverse transcription polymerase chain reaction (RT-qPCR) to identify gene expression is within range. In the embodiments of RPE cells, critical gene expressions are: RPE65 $\Delta Ct \geq -3.0$, REX1 $\Delta Ct \leq -8.0$, and geometric mean of reference genes (EIF2B2, SERF2,UBE2R2) $Ct \leq 32.0$, or comparable or similar to mature RPE cells as understood in literature.

Optional Cell Culture Improvement: Supernatant

In various embodiments, the culturing of cells have shown to produce many cellular chemical products including those used in paracrine, autocrine, endocrine, and electrical signaling between cells. These chemical products can be found in cell cultures and have potential value as a cell culture additive once extracted and categorized. Cell secretions may comprise proteins, hormones, enzymes, byproducts, waste, or a combination thereof. The raw combination of obtained factors, selected combinations thereof, or purified forms will generically be referred to as "Target Supernatant" from here on.

Further development of cell therapies aiming to replenish the lost RPE in geographic atrophy (GA) has been of great interest. One such therapy currently in phase I/IIa clinical trial includes CPCB-RPE1, a subretinal implant containing polarized human embryonic stem cell (hESC)-derived RPE (PRPE) grown on ultrathin parylene membrane (Kashani A H, Lebkowski J S, Rahhal F M, et al. A bioengineered retinal pigment epithelial monolayer for advanced, dry AMD. Sci. Transl. Med. 2018; 10: 435, eaao4097.). CPCB-RPE1 was able to restore the PRPE monolayer and support photoreceptor (PR) preservation even beyond the borders of the implant in animal studies, suggesting that PRPE-derived soluble factors play a critical paracrine role. As such, in addition to the implant itself, the unique set of essential trophic and signaling factors secreted by the polarized pigmented monolayer of PRPEs may also maintain PR survival and function.

Thus, the use of soluble trophic factors derived from PRPE cells to promote PR rescue, survival, and repair shows great promise. Several investigators have demonstrated the ability of RPE-derived conditioned medium or specific RPE trophic factors to decrease retinal cell loss in in vitro and in vivo models. Combination of growth factors and conditioned media have been reported to promote PR proliferation and differentiation in retina explants. Specifically, the use of neurotrophic growth factors such as BDNF and GDNF have been used as a supplement in transplantation of retinal sheets. As well, LaVail et al demonstrated that multiple growth factors, cytokines and neutrophins delay PR damaged in light-injury Royal Collage of Surgeon (RCS) rat models. Nonetheless, single or limited combinations of growth factors have demonstrated limited success by themselves as they only target single etiologies.

Based on the success of these studies and the paracrine effect that was observed beyond the borders of the CPCB-RPE1, it is hypothesized that the distinct concentrations of multiple trophic factors secreted by this implant, can serve as a potential combination therapy for the treatment of dry advanced non-neovascular AMD (dry AMD) in humans. The characterization, in vitro and in vivo results in animal models of retinal dystrophy treated with PRPE-soluble factors (SF) derived from CPCB-RPE1 modified implants confirmed the viability of this concept.

The method of producing a cell line specific target supernatant consists of culturing target cells with a specific cocktail of growth media between specific stages of maturation and/or different stages of differentiation on, in, or encapsulated in a biocompatible substrate or container which promotes specific growth, thereby amplifying the efficient generation of certain factors. The stages may be monitored by periodic assessment of the cells seeded on the substrate by a combination of visual morphology (e.g. cuboidal, cobblestone, pigmentation, etc.) as described above, specific tests for certain factors (e.g. BDNF, BMP-7, PEDF, TGF, VEGF, etc.) and concentrations thereof, and whole-cell current-clamp recordings to test cell resting membrane potential values (e.g. mV).

In the embodiment of RPE cells, literature has shown various indicators for differentiating between immature and mature RPE cells. For example, mature RPE cells have a resting membrane potential values typically between −40 and −50 mV. However, immature RPE calls have slightly depolarized resting membrane potentials (typically −25 to −35 mV). Further, whole-cell voltage-clamp recordings of mature RPE cells are indicative of activity of voltage-activated inward currents and voltage-gated sodium channels which are not observed in immature RPE cells (Nymark et al. 2013).

In one embodiment, RPE cells were seeded onto vitronectin coated parylene membranes and cultured in XVIVO10 (XVIVO™10, Lonza) at 37° C. in a 5% CO2 incubator. Target Supernatant (summarized in Figure X) was collected at every 4 days starting on day 28 through 40. Day 28 through day 40 was of specific interest as it embodied the specific stage of maturation of interest: near confluence (over 90%, and ideally over 98% coverage of membrane), cobblestone morphology, uniform monolayer distribution across membrane, minimal to moderate pigmentation (0%-70% pigmentation). Collection methods may vary, but in one embodiment, the medium is extracted from the culture well by pipette with care not to extract cells. In some embodiments, a cell filter may be used to ensure only the supernatant is extracted.

Further viability of the cells, and therefore the quality of secreted factors may be confirmed by USP Sterility and USP Mycoplasma testing. The cells may further be tested for gene expression by reverse transcriptase polymerase chain reaction (RT-qPCR) identifying specific genes of interest (e.g. RPE65, REX1, EIF2B2, SERF2, UBE2R2, etc. for RPE cells). The collected Target Supernatant may additionally be tested for quantities and concentrations of specific factors as outlined in Fig. X. Although there will be variations in the secreted factors by different cell lines and culturing methods, multiple samples showed minimal batch-to-batch variability of the supernatant composition if the same cell line and culturing method is used, thereby evidencing reproducibility of producing the supernatant.

In one embodiment, the collected Target Supernatant may be pooled from multiple days and/or multiple membranes. The Target Supernatant is then filtered with a 0.2 μm syringe filter system. In various embodiments, the filtered Target Supernatant may be used as is in an unconcentrated 1× form, concentrated (e.g. 3×) using Amicon centrifugal filter devices (Milipore Sigma) with a kD cut-off (e.g. 3 kD cut-off), or diluted with a diluent or drug vehicle. In several embodiments, the Target Supernatant is initially concentrated, then diluted with a specific drug vehicle (e.g. aqueous, lipophilic solution, suspension) that is elected for desired vehicle-dependent factor absorption and improved shelf-life of specific factors. The Target Supernatant is ideally stored at −80° C. until further use to extend shelf-life. The Target Supernatant may then be packaged in a syringe and optionally supplemented with growth media or other therapeutics. In another embodiment, the Target Supernatant pellet may additionally be extracted for further use as a highly concentrated or long-term diffusion implant.

In yet another embodiment, the cells may be cultured on a selectively permeable substrate to cause the cells to become polarized and generate specific secretions. For example, polarized RPE cells are known to produce apical secretions, basal secretions, and non-polar specific secretions. RPE cell apical secretions comprise αB Crystallin, Hyaluronan, MMP-9, PEDF, TGF-β, TIMP-I, MGF-E8. RPE cell basal secretions comprise: Cystatin C, Endothelin I, FGF 5, VEGF. RPE cell non-polar specific secretions comprise: BDNF, CFH, CNTF, Fibulin 3/5, FGF 2, HB-EGF, HGF, IGF-I, LIF, MMP-9, NGF, Tropoelastin. Other trophic factors identified are: IGFBP-2, IGFBP-3, IGFBP-6, PEDF-AA, BMP-7.

The packaged supernatant may be injected periodically into the target site as a therapy with or without being an additional supplement after implantation of a cellular therapy medium (e.g. cellular solution, cell seeded gel, cell seeded substrate, etc.) to supplement the support of growth, continued functionality, and integration of host and or implanted cells with the target site tissue. The packaged supernatant may additionally be coated onto the cellular therapy medium prior to implantation, added to culture media, or coated onto the substrate prior to cell seeding.

In other embodiments, after the addition of the supernatant, the cells are further cultured until they exhibit mature characteristics. For RPE cells, these mature characteristics are selected from: (i) pigmented RPE cells, (ii) polarized RPE cells, (iii) RPE cells with mature cobblestone morphology with no neural or fibroblastic cell regions, (iv) RPE cells with gene expression levels of mature cells, and (v) RPE cells in a confluent monolayer configuration.

In embodiments when the cell seeded support structure will not be implanted, various other cell growth surfaces may be used including substrates, a lattice structure, agar, a hydrogel, or other cell growth surfaces known in the art.

The supernatant has shown therapeutic activity in animal models (i.e. immunodeficient Royal College of Surgeons (iRCS) rat models, an accepted FDA animal model for drug and cell therapeutic development for geographic atrophy and age-related macular degeneration) including anti-inflammatory, visual function response (i.e. increased b-wave amplitude assessed by electroretinogram), and preserved retinal architecture including increased photoreceptor survival and function. Furthermore, the supernatant shows greater photoreceptor survival compared to the single factor of PEDF control, a known neuroprotective and anti-angiogenic agent, indicating that more than one factor contributes to the target paracrine effect. Further, no evidence of tumorigenicity or endophthalmitis was observed despite numerous injections.

Optimized Cryopreservation Protocol and Considerations
Cryo-Hibernation Protocol In some embodiments, alternative to standard cryopreservation protocols, cryo-hibernation protocols have shown increased viability of thawed cell seeded on substrates. Cryo-hibernation protocol is as follows. Following the initial controlled temperature ramp-down phase, once a first temperature below the latent heat release of the seeded cells is reached (between 0° C. and −20° C.) the cells are kept at the first temperature for a first period of time. The first temperature is any temperature below the latent heat release temperature and may be −20, −30, −40, −50, −60, −70, −80, −90, or −100° C. The first period of time is 12 hours, 1 day, 7 days, 28 days and helps acclimate the cells to a cryopreserved state without immediate drastic changes to the temperature. This acclimatization additionally prevents microtears from forming in substrates as may be caused by of temperature reduction (−1° C./min or greater). After the first period of time, the cryopreserved cells are transferred and maintained at a storage temperature for a second period of time. In most cases, the storage temperature is −196° C. (e.g. temperature of liquid nitrogen) for convenience, but may be the same temperature as the hibernation temperature. In some embodiments, transferring the cell-seeded substrate to a second temperature is also conducted with a controlled temperature ramp-down phase temperature reduction rate of from about −1° C. per minute to about −30° C. per minute or any rate within this range, until the second temperature is obtained. This specific ramp down of temperature aids in uniform temperature reduction of the various components (i.e. the substrate, at least one cell type, the cryoprotectant solution, and the cryopreservation container).

In certain embodiments, the cells are kept in set temp freezers and carrying cases at the first temperature until thawing. Although this will require a portable set temp freezer, long term hibernation temperatures increases cell viability post-thaw as the thawing process has a smaller temperature differential than that from −196° C. (e.g. temperature of liquid nitrogen), and thereby has significantly less temperature variation zones which causes variable ice crystal formation patterns and differing cryoprotectant removal rates for batch cell seeded substrate thawing as well as within each individual substrate on a smaller scale.

Cryopreservation Optimization: RPE Cell Lines

In certain embodiments of hESC-RPE cells, various combinations of cryopreservation protocols were tested and optimized for the specific cell line. Although tested with a specific cell line, similar outcomes are anticipated for other RPE cell lines as major factors of cell line and substrate characteristics as described above were taken into consideration.

The RPE cells of CPCB-RPE1 implants had shown cell optimal cryopreservation viability characteristics include: (i) non-pigmented RPE cells (including depigmented RPE cells), (ii) non-polarized or partially polarized RPE cells, (iii) majority of RPE cells with mature cobblestone morphology, (iv) RPE cells with gene expression levels below that of mature cells or lacking specific gene expression, (v) RPE cells in a subconfluent monolayer configuration, or a combination thereof. This combination of cell optimal cryopreservation viability characteristics were obtained between 3-12 days (7 days being the median day between batches) after seeding onto the implantable substrate.

The CPCB-RPE1 cell line had shown substrate optimal cryopreservation viability characteristics including the coefficient of thermal expansion of the substrate, a substrate elasticity parameter, substrate thickness, and substrate implantation size, all of which were taken into account for the substrate design.

Various cell lines were tested with various combinations of cryoprotective agents and freezing rates. The most viable combination was the use of CS-10 (manufacturer: BioLife Solutions, Bothell, Wash.) having a DMSO concentration of 10%, and freezing between the ranges of −5° C./min and −30° C./min. Comparatively, DMSO concentrations of 2% and 5% as well as freezing rates between −1 C and −3 C have lower cell viability outcomes.

The combinations were then assessed using various methods including, phase contrast images of cells 1 day and 1 week post thaw, gene expression of cells, viability staining and alamar blue metabolism of cells.

| Trophic Factors | Biological Effect | Mean (pg/ml) ± SD |
| --- | --- | --- |
| BDNF | BDNF should only be neurotrophic. | 45 ± 10 |
| BMP-7 | Anti-inflammatory, BMP-7 reverses fibrosis and EMT through reduction in monocyte infiltration into inflamed tissue. | 491 ± 129 |
| NGF□ | Neurotrophic, inflammation | 181 ± 39 |
| GDF-15 | Regulating apoptosis, cell repair and cell growth | 504 ± 102 |
| IGFBP-2 | Anti-inflammatory | 9934 ± 748 |
| IGFBP-3 | | 152,279 ± 16,038 |
| IGFBP-6 | | 6938 ± 554 |
| LIF | Photoreceptor rescue, RPE survival | 72.8 ± 3.24 |
| PEDF□ | Anti-angiogenic, neurotrophic | 20.98 ± 0.66 |
| PDGF- | Potent mitogen for cells of | 3032 ± 780 |

-continued

| Trophic Factors | Biological Effect | Mean (pg/ml) ± SD |
|---|---|---|
| AA | mesenchymal origin, including fibroblasts and glial cells. | |
| TGF□1 | Anti-inflammatory | 89,442 ± 14,405 |
| VEGF | Pro-angiogenic, photoreceptor development | 902 ± 34 |

Example Concentrations of Select Trophic Factors in a 3× Purified Supernatant

The term "substantially" or "approximately" means±10% (e.g., by weight or by volume), and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

What is claimed is:

1. A method of cryopreserving cells on a substrate, the method comprising:
   providing a biocompatible polymer substrate seeded with a monolayer of immature retinal pigment epithelium (RPE) cells, the polymer substrate providing a cell seeding surface;
   identifying when i) the monolayer of immature RPE cells reaches between 90% and 99% confluence on the substrate and ii) most of the immature RPE cells are not fully pigmented; and
   exposing the monolayer of RPE cells that are between 90% and 99% confluent to a controlled temperature reduction rate between about −1° C. per minute to about −30° C. per minute until a first temperature below −20° C. is reached.

2. The method of claim 1, wherein the cell-seeded substrate reaches a temperature below that which delineates a latent heat release of the seeded cells.

3. The method of claim 2, wherein a surface of the substrate is substantially parallel to the monolayer of the immature RPE cells seeded on the substrate, sufficient to induce nucleation and efficient temperature compensation in response to the latent heat release of the seeded cells.

4. The method of claim 1, further comprising:
   maintaining the cell-seeded substrate at the first temperature, the first temperature being between −20° C. to about −100° C. after the controlled temperature reduction rate for a first period of time to obtain uniformity of temperature; and
   maintaining the cells at a storage temperature lower than the first temperature for a second period of time within 50° C. of the first temperature, thereby obtaining cryopreserved cells.

5. The method of claim 1, further comprising:
   maintaining the cell-seeded substrate at the first temperature, the first temperature being between −20° C. to about −100° C. after the controlled temperature reduction rate for a first period of time; and
   conducting a second controlled temperature reduction rate to finally maintain the cells at a storage temperature below −196° C. for a second period of time, thereby obtaining cryopreserved cells.

6. The method of claim 5, wherein the second period of time is between 24 hours and 60 months.

7. The method of claim 5, wherein the second controlled temperature reduction rate is between about −1° C. per minute to about −30° C. per minute.

8. The method of claim 1, wherein the monolayer of cells has a cell seeding density between 200,000 and 700,000 cells per milliliter of cell suspension, or between 100,000 and 350,000 cells per square centimeter of substrate surface.

9. The method of claim 1, wherein over 50% of the RPE cells have a cobblestone morphology.

10. The method of claim 1, wherein the RPE cells have no pigmentation or only partial pigmentation.

11. The method of claim 1, wherein the monolayer of RPE cells exhibit cryopreservation viability characteristics selected from: adhered but non-polarized, partially polarized, or fully polarized RPE cells, RPE cells with or without mature cobblestone morphology, RPE cells with gene expression levels below that of mature cells or lacking specific gene expression of mature cells.

12. The method of claim 1, wherein the substrate has one or more characteristics selected from: (i) a coefficient of thermal expansion of the substrate, (ii) a substrate elasticity parameter, (iii) a substrate thickness, (iv) surface modification, (v) shear force resistance, said characteristics helping to enhance viability of the seeded cells and functionality of the substrate during cryopreservation and thawing.

13. The method of claim 1, wherein the biocompatible polymer substrate comprises parylene.

14. The method of claim 1, further comprising:
   determining when at least one or more apical secretions, basal secretions, or non-polar specific secretions of the immature RPE cells are at levels below that of mature RPE cells.

15. The method of claim 14, wherein the apical secretions comprise αB crystallin, hyaluronan, matrix metallopeptidase (MMP)-9, pigment epithelium-derived factor PEDF), transforming growth factor (TGF)-β, tissue inhibitors of metalloproteinases (TIMP)-I, or mechano growth factor (MGF)-E8.

16. The method of claim 14, wherein the basal secretions comprise cystatin C, endothelin I, fibroblast growth factor (FGF) 5, or vascular endothelial growth factor (VEGF).

17. The method of claim 14, wherein the non-polar specific secretions comprise brain-derived neurotrophic factor (BDNF), complement factor H (CFH), ciliary neurotrophic factor (CNTF), fibulin 3/5, fibroblast growth factor (FGF) 2, heparin binding-epidermal growth factor (HB-EGF), hepatocyte growth factor (HGF), insulin-like growth factor (IGF)-I, leukemia inhibitory factor (LIF), matrix metalloproteinase (MMP)-9, nerve growth factor (NGF), or Tropoelastin.

18. The method of claim 1, further comprising:
   determining gene expression of the immature RPE cells of at least one or more of RPE65, REX1, EIF2B2, SERF2, UBE2R2 to be below that of mature RPE cells.

19. The method of claim 1, wherein the substrate comprises thin regions configured to allow the cells to diffuse nutrients therethrough.

20. A method of generating an implantable cell seeded substrate, the method comprising:

providing a biocompatible polymer substrate seeded with a monolayer of immature retinal pigment epithelium (RPE) cells, the polymer substrate providing a cell seeding surface;

cryopreserving cells that are between 90% and 99% confluent on the substrate by exposing the substrate seeded with cells to a controlled temperature reduction rate between about −1° C. per minute to about −30° C. per minute;

transferring the cell seeded substrate to a temperature below 4° C., thereby obtaining cryopreserved or hibernated cells;

thawing the cryopreserved cells on said substrate by warming the cell seeded substrate to a target temperature using a temperature ramp-up heating rate to obtain thawed cells seeded on the substrate, wherein the thawed cells retain viability and/or functionality post-thaw; and culturing the seeded cells in a first medium comprising a basal medium supplemented with a combination of consisting of at least one or more of bovine serum albumin (BSA), activin A, hepatocyte growth factor (FGF), insulin-like growth factor (IGF) 1, Dickkopf-related protein 1 (DKK1), and noggin.

* * * * *